US012570620B2

(12) United States Patent
Gray et al.

(10) Patent No.: US 12,570,620 B2
(45) Date of Patent: Mar. 10, 2026

(54) COVALENT INHIBITORS OF CREATINE KINASE (CK) AND USES THEREOF FOR TREATING AND PREVENTING CANCER

(71) Applicant: Dana-Farber Cancer Institute, Inc., Boston, MA (US)

(72) Inventors: Nathanael S. Gray, Boston, MA (US); Edward Chouchani, Boston, MA (US); Tinghu Zhang, Brookline, MA (US); Narek Darabedian, Boston, MA (US); Wenzhi Ji, Boston, MA (US); Jianwei Che, Sharon, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 420 days.

(21) Appl. No.: 18/033,269

(22) PCT Filed: Oct. 22, 2021

(86) PCT No.: PCT/US2021/056280

§ 371 (c)(1),
(2) Date: Apr. 21, 2023

(87) PCT Pub. No.: WO2022/087433

PCT Pub. Date: Apr. 28, 2022

(65) Prior Publication Data

US 2023/0399304 A1 Dec. 14, 2023

Related U.S. Application Data

(60) Provisional application No. 63/104,963, filed on Oct. 23, 2020.

(51) Int. Cl.

| | |
|---|---|
| ***C07D 265/36*** | (2006.01) |
| ***C07D 217/24*** | (2006.01) |
| ***C07D 401/12*** | (2006.01) |
| ***C07D 413/04*** | (2006.01) |
| ***C07D 413/06*** | (2006.01) |
| ***C07D 413/12*** | (2006.01) |
| ***C07D 498/04*** | (2006.01) |
| ***C07F 9/6533*** | (2006.01) |

(52) U.S. Cl.

CPC ......... *C07D 265/36* (2013.01); *C07D 217/24* (2013.01); *C07D 401/12* (2013.01); *C07D 413/04* (2013.01); *C07D 413/06* (2013.01); *C07D 413/12* (2013.01); *C07D 498/04* (2013.01); *C07F 9/65335* (2013.01)

(58) Field of Classification Search

CPC .. C07D 265/36; C07D 217/24; C07D 401/12; C07D 413/04; C07D 413/06; C07D 498/04; C07F 9/65335

See application file for complete search history.

(56) References Cited

U.S. PATENT DOCUMENTS

| | | | | |
|---|---|---|---|---|
| 2,554,737 | A | 5/1951 | Franz et al. | |
| 3,547,915 | A | 12/1970 | Bub | |
| 5,141,935 | A | 8/1992 | Takenaka et al. | |
| 5,420,126 | A | 5/1995 | Matsumoto et al. | |
| 2021/0317140 | A1 * | 10/2021 | Rai ...................... | C07D 487/04 |

FOREIGN PATENT DOCUMENTS

| | | | |
|---|---|---|---|
| GB | 1137796 | A | 12/1968 |
| WO | WO-1999/052875 | A1 | 10/1999 |
| WO | WO-2006/078697 | A1 | 7/2006 |
| WO | WO-2010/139481 | A1 | 12/2010 |
| WO | WO-2011/048148 | A2 | 4/2011 |
| WO | WO-2014/149164 | A1 | 9/2014 |
| WO | WO-2015/058084 | A1 | 4/2015 |
| WO | WO-2015/108992 | A1 | 7/2015 |
| WO | 2020/023340 | A1 | 1/2020 |
| WO | 2020/081572 | A1 | 4/2020 |
| WO | WO-2022/087433 | A1 | 4/2022 |

OTHER PUBLICATIONS

Bertron et al., "The discovery of VU0486846: steep SAR from a series of M1 PAMs based on a novel benzomorpholine core," Bioorg Med Chem Lett, 28(12): 2175-2179 (2018).

Davies et al., "181: Reactions of ethylene oxides. Part IV. The reaction of epichlorohydrin with some aromatic amines," J Chem Soc, (890-894) (1950).

International Search Report and Written Opinion for International Application No. PCT/US2021/056280 mailed Dec. 20, 2021.

Resnick et al., "Rapid Covalent-Probe Discovery by Electrophile-Fragment Screening," J Am Chem Soc, 141(22): 8951-8968 (2019).

Santangelo et al., "Synthesis and positive inotropic effect of 1-alkyl-and 1 acyl-6,7-dimethoxy-3-dimethylamino-1,2,3,4-tetrahydroquinolines," Eur J Med Chem, 29(11): 877-882 (1994).

Ye et al., "Synthesis and Crystal Structure of Novel N-Acyl-2,3-Dimethyl-3,4-2H-1,4 Benzoxazine," J Chem Res, 39(6): 357-359 (2015).

(Continued)

*Primary Examiner* — Timothy R Rozof

(74) *Attorney, Agent, or Firm* — Nielsen IP Law LLC

(57) ABSTRACT

The present disclosure relates to compounds that are capable of inhibiting creatine kinase. The present disclosure also relates to methods of treating cancer, such as hematological malignancies.

12 Claims, 10 Drawing Sheets

(56) References Cited

OTHER PUBLICATIONS

Communication pursuant to Article 94(3) EPC, EP Application No. 21807447.4, dated Sep. 17, 2024, 5 pages.
First Office Action and Search Report, CN Application No. 202180071306.4, dated Apr. 30, 2025, 12 pages.
CAS No. 1156153-91-1, 2 pages.
CAS No. 923253-62-7, 2 pages.
Shigematsu, H. et al., Clinical and Biological Features Associated With Epidermal Growth Factor Receptor Gene Mutations in Lung Cancers, JNCI: Journal of the National Cancer Institute, Mar. 2, 2005, 339-346, 97, 5.
Buttitta, F. et al., Mutational analysis of the HER2 gene in lung tumors from Caucasian patients: Mutations are mainly present in adenocarcinomas with bronchioloalveolar features, Dec. 1, 2006, 2586-2591, 119, 11.
Tomizawa, . et al., Prognostic and predictive implications of HER2/ERBB2/neu gene mutations in lung cancers, Lung Cancer, Oct. 2011, 139-144, 74(1).
Mazieres, J. et al., Lung Cancer That Harbors an HER2 Mutation: Epidemiologic Characteristics and Therapeutic Perspectives, Journal of Clinical Oncology, 2013, 8 pages, 31, 16.
Li, X. et al., Epidemiological study of HER-2 mutations among EGFR wild-type lung adenocarcinoma patients in China, BMC Cancer, 2016, 828, 16.
Slamon, D. J. et al., Human Breast Cancer: Correlation of Relapse and Survival with Amplification of the HER-2/neu Oncogene, Science, 1987, 177-182, 235, 4785.
Slamon, D. J. et al., Studies of the HER-2/neu Proto-Oncogene in Human Breast and Ovarian Cancer, Science, 1989, 707-712, 244, 4905.
Shigematsu, H. et al., Somatic mutations of the HER2 kinase domain in lung adenocarcinomas, Cancer Res, 2005, 1642-1646, 65, 5.
Kris, M. G. et al., Using multiplexed assays of oncogenic drivers in lung cancers to select targeted drugs, JAMA, 2014, 1998-2006, 311, 19.
De Grève, J et al., Clinical activity of afatinib (BIBW 2992) in patients with lung adenocarcinoma with mutations in the kinase domain of HER2/neu, Lung Cancer, 2012, 123-127, 76, 1.
Kris, M. G., et al., Targeting HER2 aberrations as actionable drivers in lung cancers: phase II trial of the pan-HER tyrosine kinase inhibitor dacomitinib in patients with HER2-mutant or amplified tumors, Annals of Oncology, 2015, 1421-1427, 26, 7.
Gandhi, et al., Phase I Study of Neratinib in Combination with Temsirolimus in Patients with Human Epidermal Growth Factor Receptor 2-dependent and Other Solid Tumors, Journal of Clinical Oncology, 2014, 68-75, 32, 2.
Mazières, J et al., Lung cancer patients with HER2 mutations treated with chemotherapy and HER2-targeted drugs: results from the European EUHER2 cohort, Annals of Oncology, 2016, 281-286, 27, 2.
Eng, J. et al., Outcomes of chemotherapies and HER2 directed therapies in advanced HER2-mutant lung cancers, Lung Cancer, 2016, 53-56, 99.

* cited by examiner

COVALENT INHIBITORS OF CREATINE KINASE (CK) AND USES THEREOF FOR TREATING AND PREVENTING CANCER

RELATED APPLICATIONS

This application is the § 371 National Stage of PCT/US2021/056280, filed Oct. 22, 2021, which claims the benefit of priority to U.S. Provisional Patent Application No. 63/104,963, filed on Oct. 23, 2020, the contents of each of which are fully incorporated by reference herein.

BACKGROUND

Creatine kinase (CK), also known as creatine phosphokinase (CPK) or phosphocreatine kinase is involved in regulating cell energy levels through conversion of phosphocreatine (PCr) and adenosine diphosphate (ADP) to adenosine triphosphate (ATP). Creatine kinase has been implicated in certain cancers, such as lung cancer, liver cancer, colon cancer, pancreatic, or blood cancers. Together, the aforementioned group of cancers represents a significant portion of all cancer cases in the both the United States and the world. For instance, there are approximately 228,000 cases of lung cancer in the United States per year. Accordingly, there is an ongoing unmet need for new cancer therapies.

SUMMARY OF THE INVENTION

In one aspect, the present disclosure provides compounds of Formula I:

I

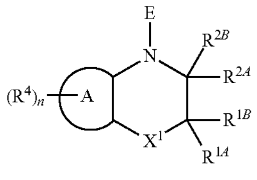

or a pharmaceutically acceptable salt thereof, wherein

A is a five or six membered aryl or heteroaryl ring;

E is an electrophile;

$X^1$ is a bond, O, $NR^{3A}$, $CR^{3A}R^{3B}$, or S;

$R^{1A}$ is alkyl, alkyloxy, cycloalkyloxy, aryloxy, heteroaryloxy, amino, cycloalkyl, heterocyclyl, aryl, heteroaryl, aralkyl, heteroaralkyl, acyl, amide, ester, urea, or carbamate; or $R^{1A}$ and $R^{1B}$ combine to form a cycloalkyl or heterocyclyl;

$R^{1B}$, $R^{2A}$, $R^{2B}$, $R^{3A}$, and $R^{3B}$ are each independently selected from H, alkyl, aralkyl, acyl, amide, carboxyl, ester, and carbamate;

$R^4$ is alkyl, alkenyl, alkynyl, halo, hydroxyl, carboxyl, acyl, acetyl, ester, thioester, alkoxy, phosphoryl, amino, amide, cyano, nitro, azido, alkylthio, cycloalkyl, cycloalkylalkyl, heterocyclylalkyl, heteroaralkyl, sulfonamide, aryl, heteroaryl, heterocyclyl, or aralkyl; and n is 0-5.

In another aspect, the present disclosure provides pharmaceutical compositions comprising a compound of the disclosure.

In certain aspects, the present disclosure provides methods of treating cancer in a subject in need therefore, comprising administering a compound of the disclosure or a pharmaceutically acceptable salt thereof to the subject.

DETAILED DESCRIPTION OF THE INVENTION

Figure 1:
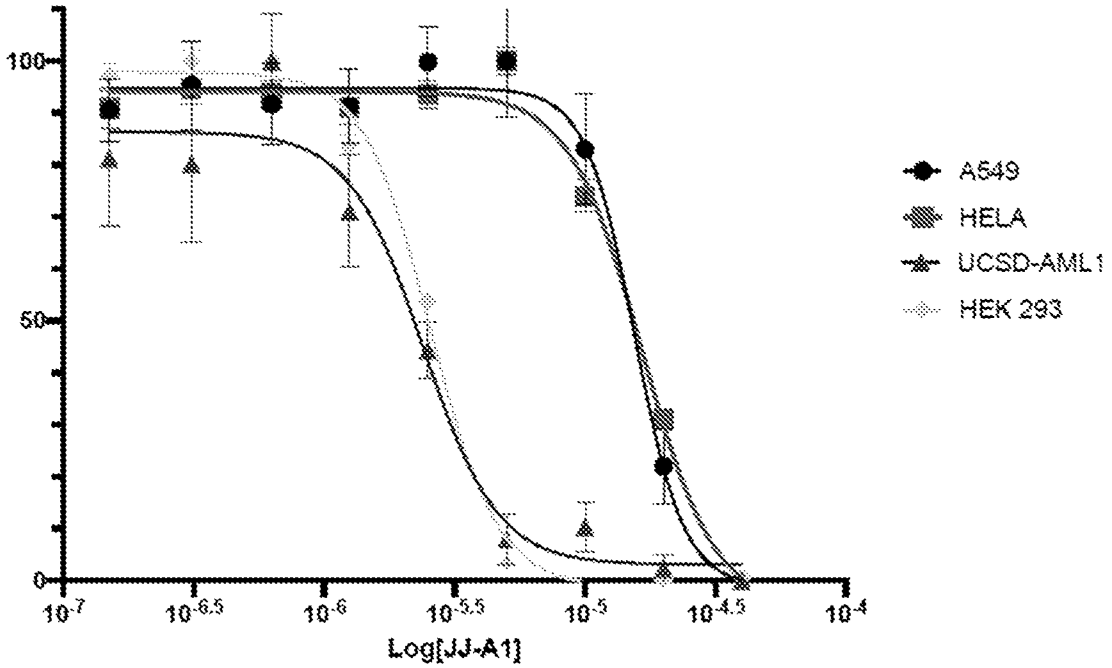
FIG. 1 shows the activity of JJ-A1 against certain cell lines.
Figure 2A:
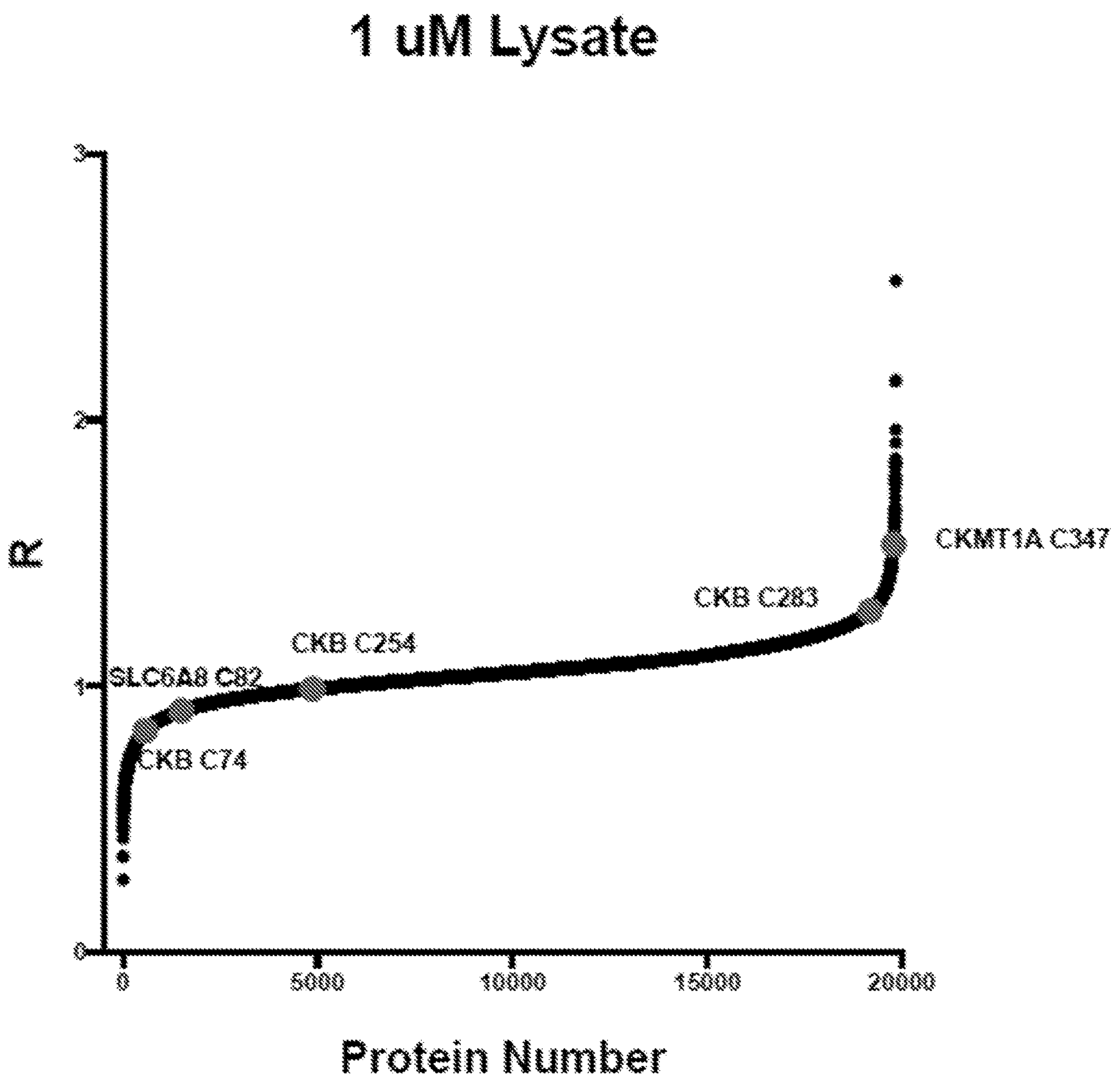
FIGS. 2A-2F show the selectivity of JJ-A1 against certain creatine kinase isoforms.
Figure 2B:
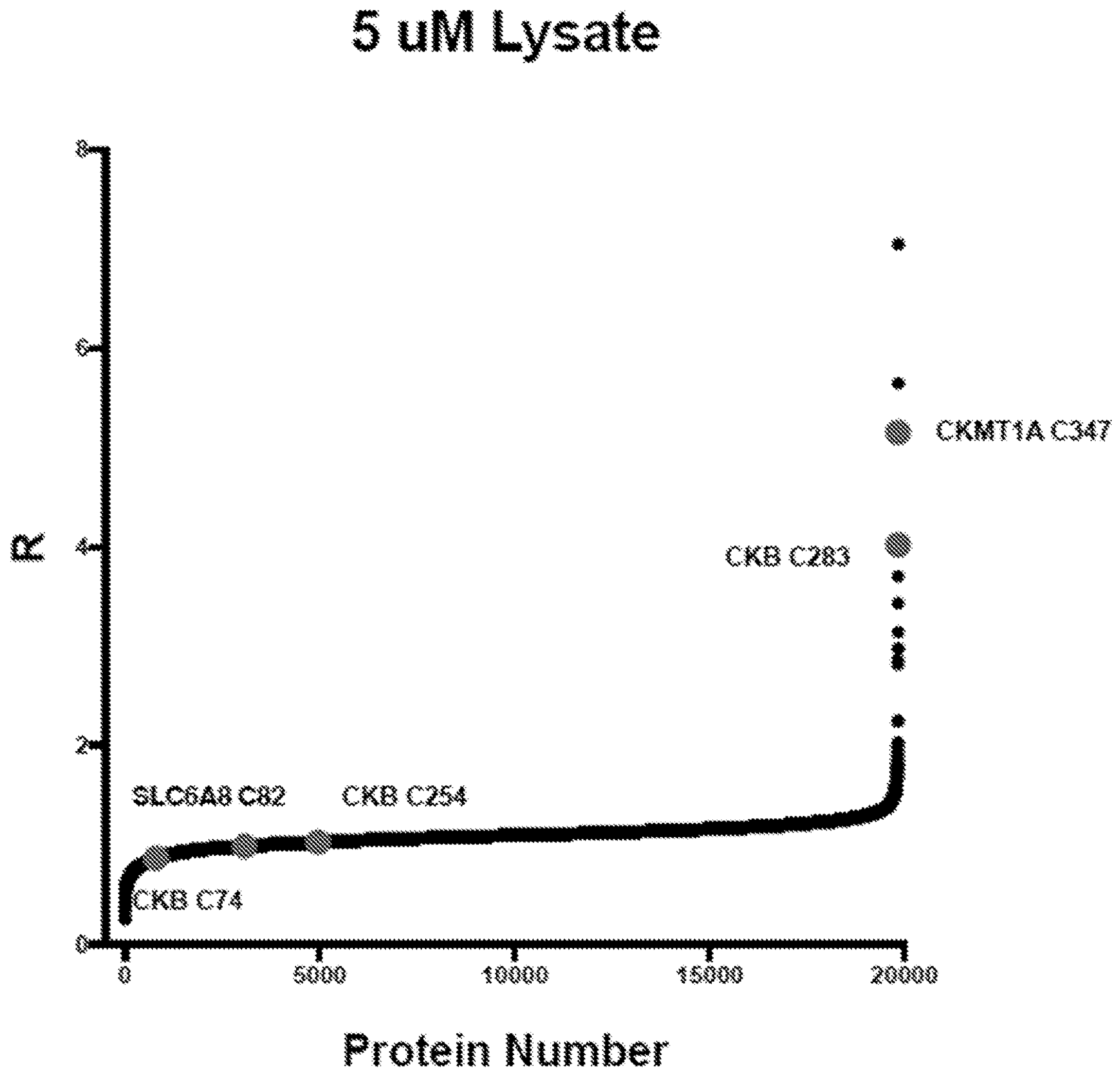
Figure 2C:
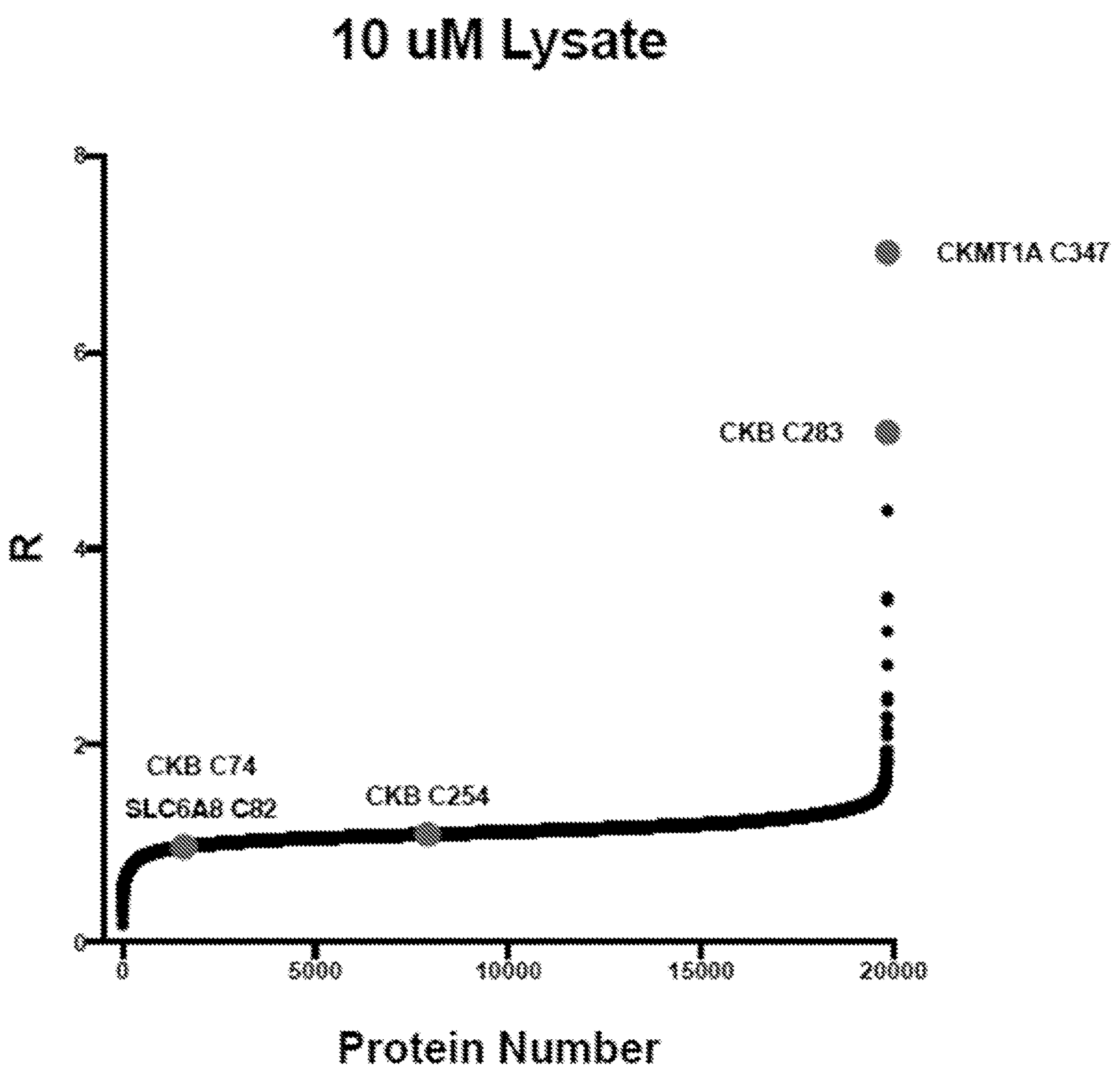
Figure 2D:
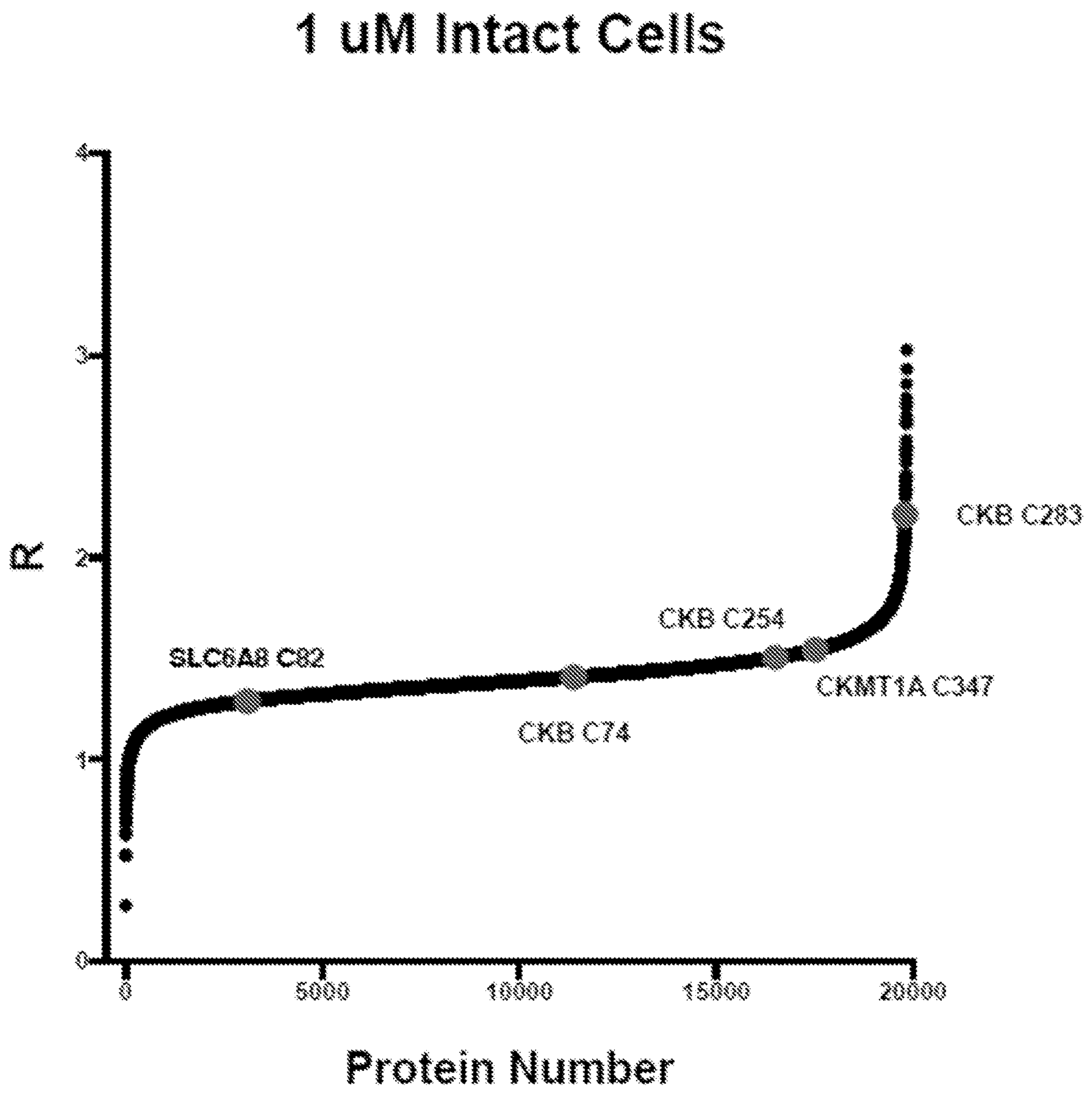
Figure 2E:
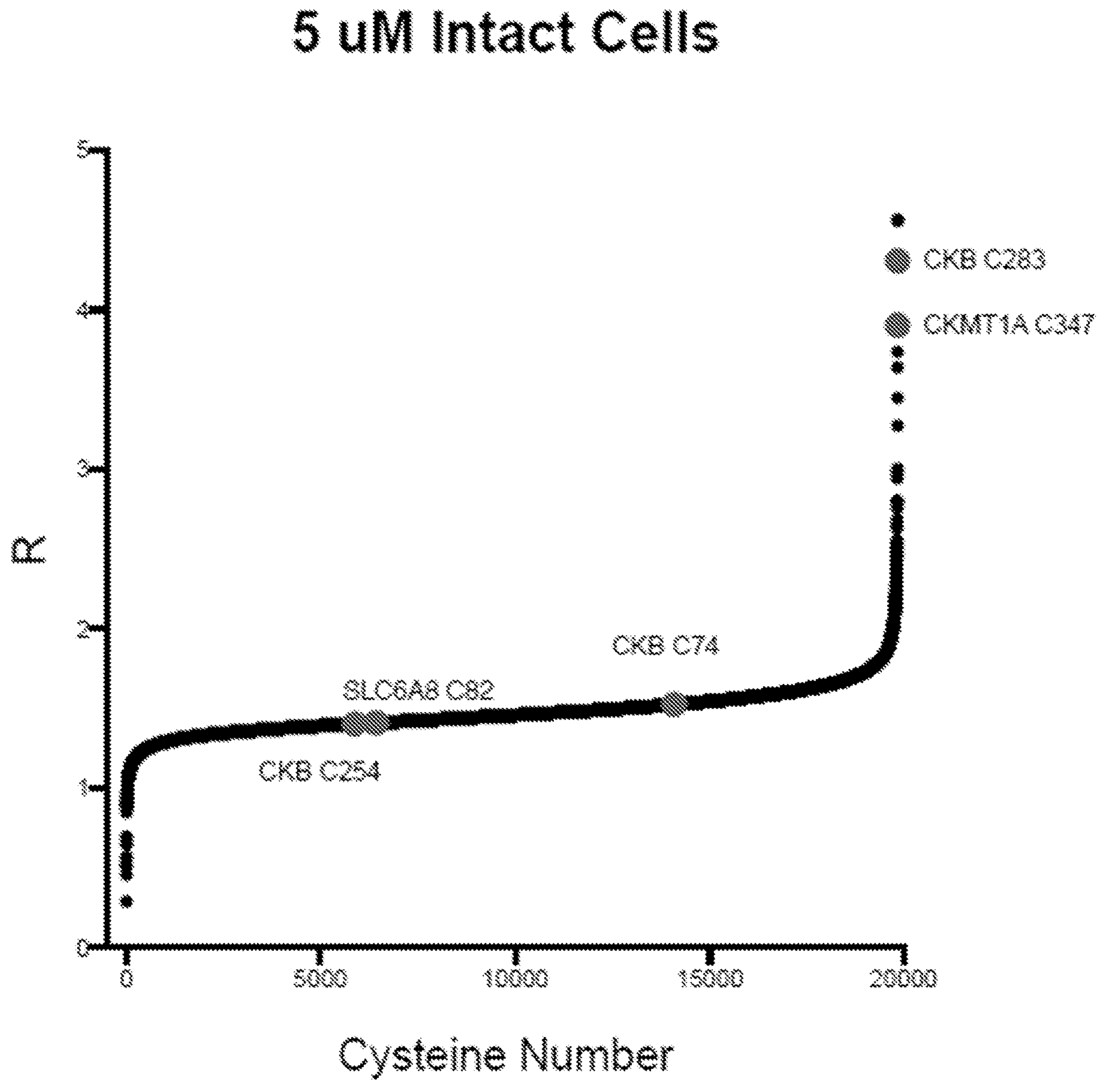
Figure 2F:
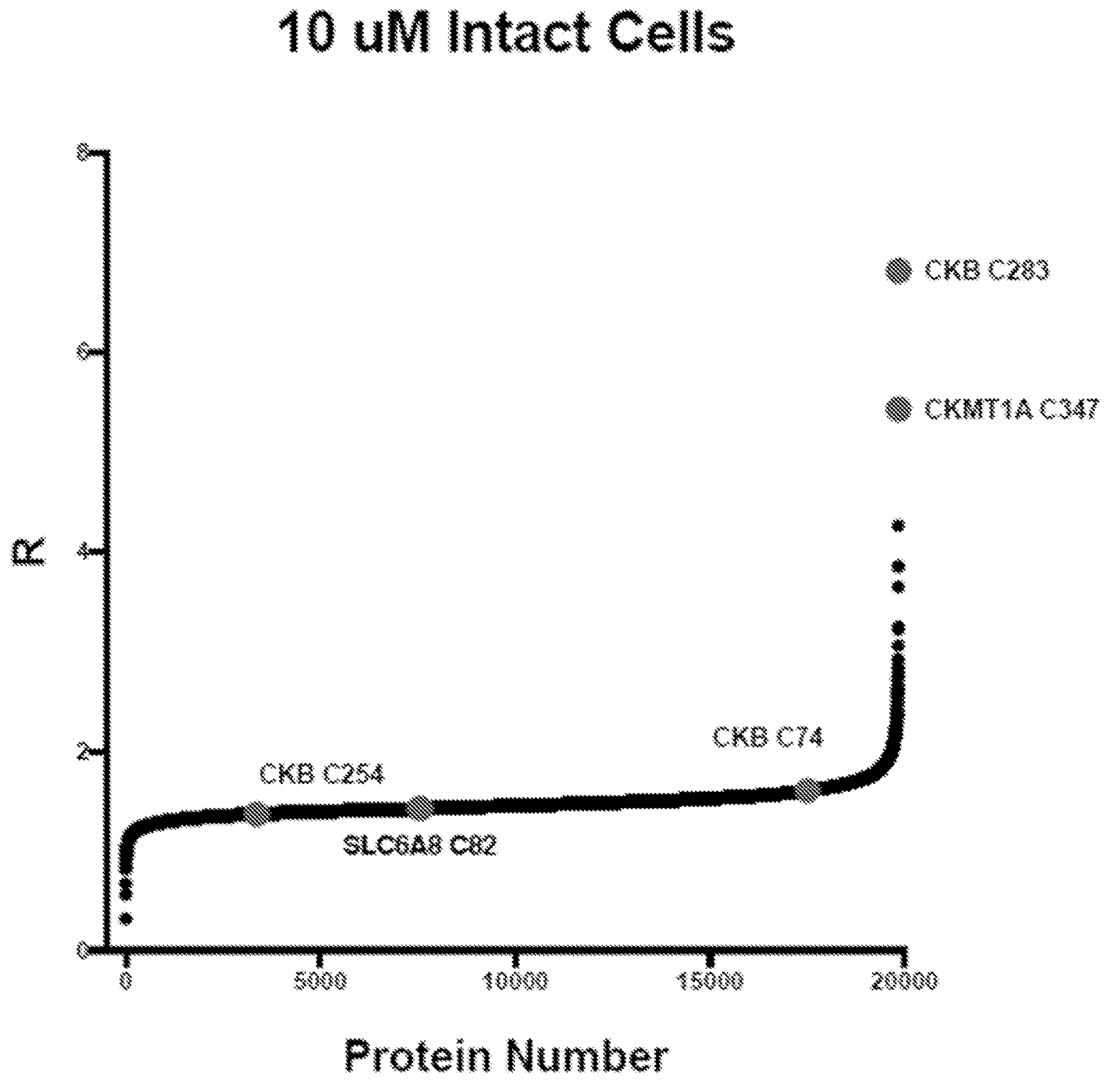
Figure 3A:
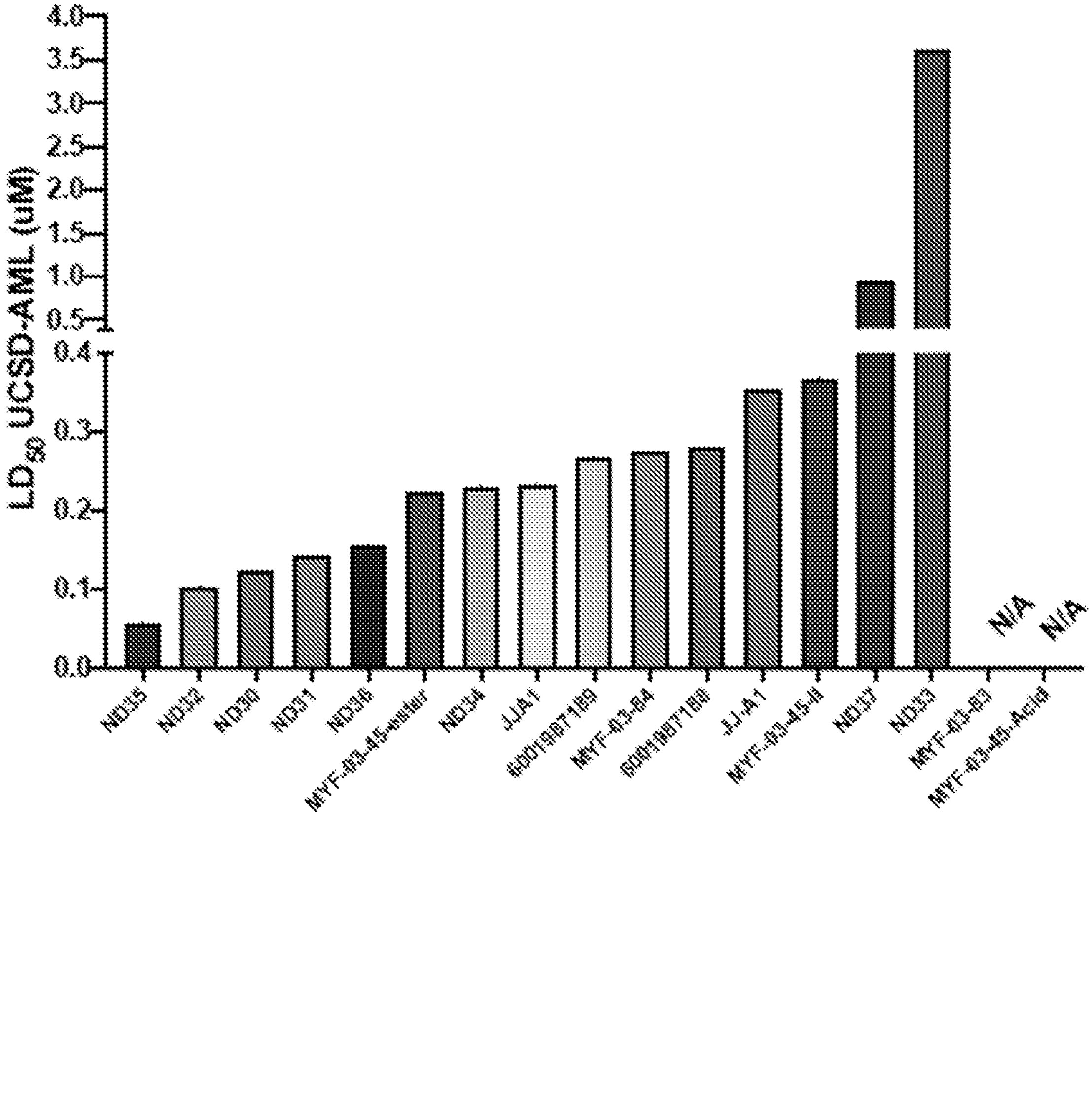
FIG. 3A shows the $IC_{50}$ of certain compounds of the disclosure against recombinant creatine kinase blood (CKB).
Figure 3B:
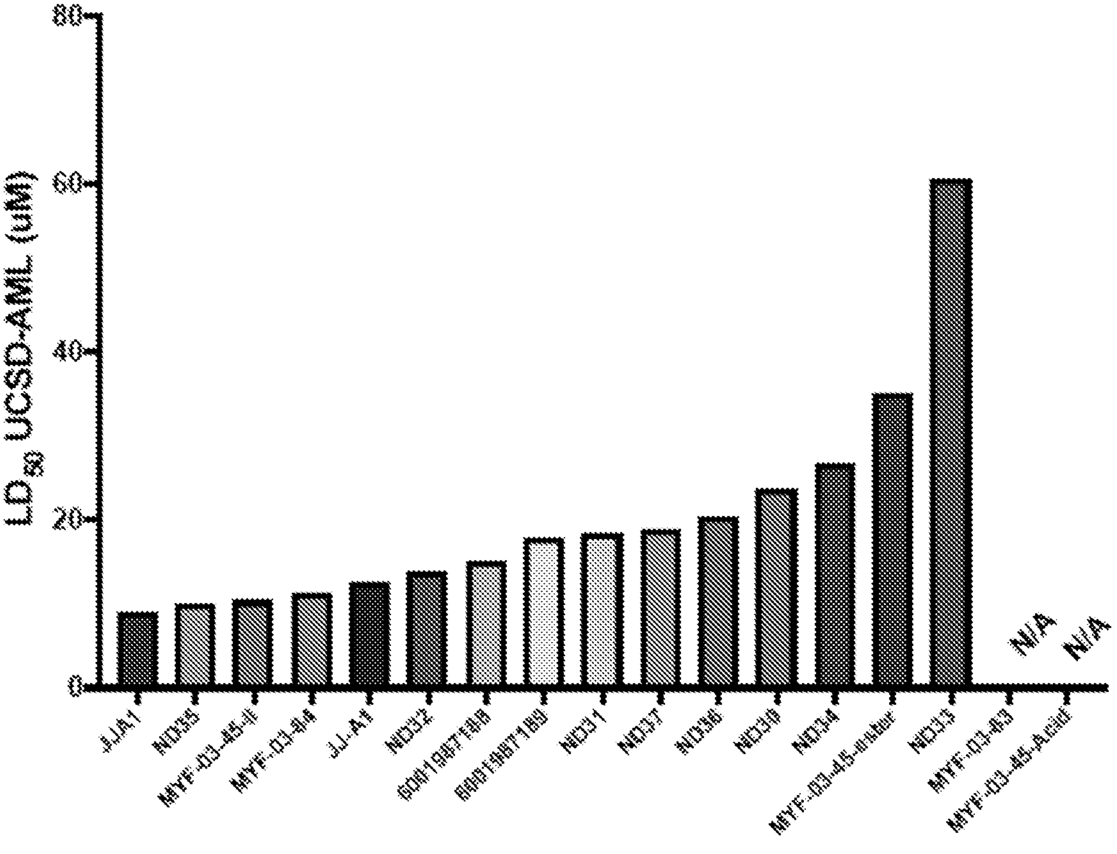
FIG. 3B shows the $LD_{50}$ of certain compounds of the disclosure against UCSD-AML1 cells.
Figure 3C:
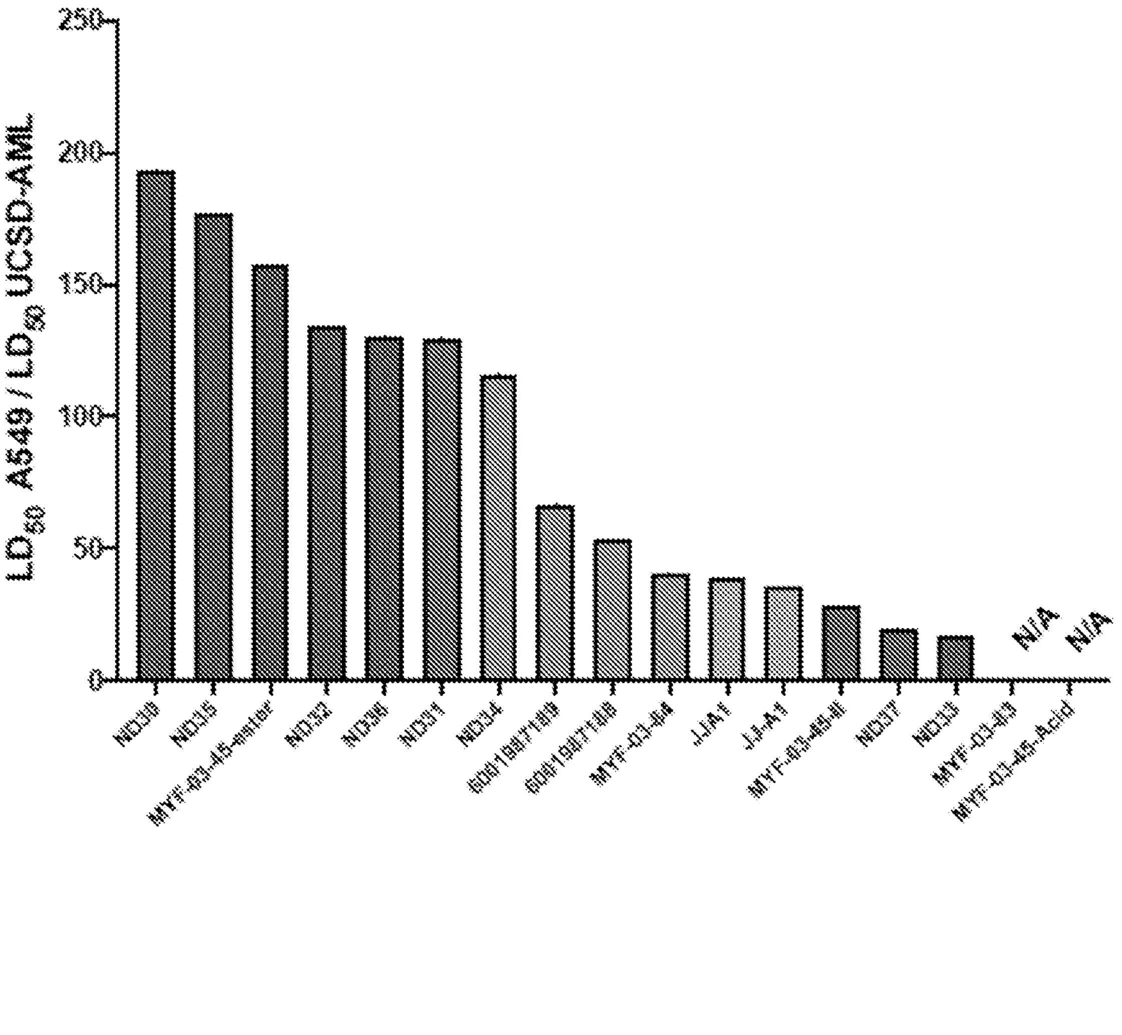
FIG. 3C shows the $LD_{50}$ of certain compounds of the disclosure against A549 cells.

Although reversible small molecule inhibitors of certain protein kinases have been extensively investigated, irreversible kinase inhibitors remain underexplored. Compared to their reversible counterparts, irreversible kinase inhibitors offer significant advantages, including increased potency and selectivity, longer residence times, the ability to inhibit kinases with existing resistance mutations, and non ATP-competitive modes of action. Despite these advantages, irreversible kinase inhibitors have only been developed for a handful of kinases. Disclosed herein are irreversible inhibitors of creatine kinase.

In one aspect, the present disclosure provides compounds of Formula I:

I

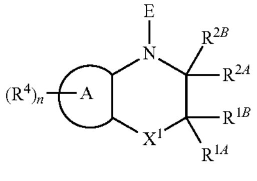

or a pharmaceutically acceptable salt thereof, wherein

A is a five or six membered aryl or heteroaryl ring;

E is an electrophile;

$X^1$ is a bond, O, $NR^{3A}$, $CR^{3A}R^{3B}$, or S;

$R^{1A}$ is alkyl, alkyloxy, cycloalkyloxy, aryloxy, heteroaryloxy, amino, cycloalkyl, heterocyclyl, aryl, heteroaryl, aralkyl, heteroaralkyl, acyl, amide, ester, urea, or carbamate; or $R^{1A}$ and $R^{1B}$ combine to form a cycloalkyl or heterocyclyl;

$R^{1B}$, $R^{2A}$, $R^{2B}$, $R^{3A}$, and $R^{3B}$ are each independently selected from H, alkyl, aralkyl, acyl, amide, carboxyl, ester, and carbamate;

$R^4$ is alkyl, alkenyl, alkynyl, halo, hydroxyl, carboxyl, acyl, acetyl, ester, thioester, alkoxy, phosphoryl, amino, amide, cyano, nitro, azido, alkylthio, cycloalkyl, cycloalkylalkyl, heterocyclylalkyl, heteroaralkyl, sulfonamide, aryl, heteroaryl, heterocyclyl, or aralkyl; and n is 0-5.

In certain embodiments, the compound is not
JJ-A1
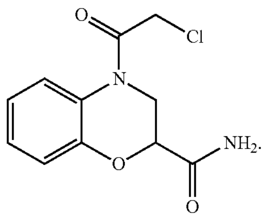
In certain embodiments, the electrophile has a structure represented by any one of the following formula:
(i-1)
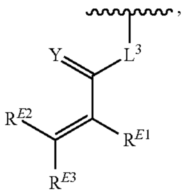
(i-2)
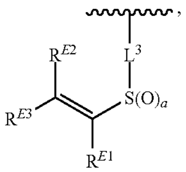
(i-3)
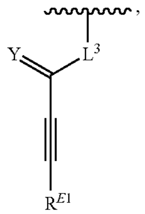
(i-4)
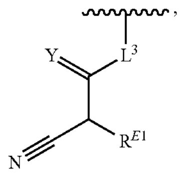
(i-5)
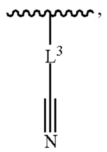
(i-6)
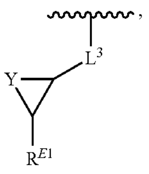
-continued
(i-7)
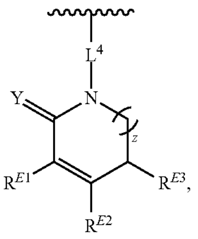
(i-8)
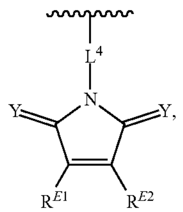
(i-9)
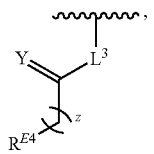
(i-10)
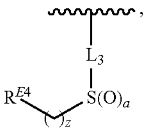
(i-11)
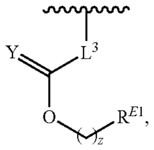
(i-12)
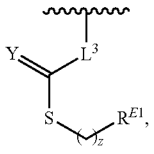
(i-13)
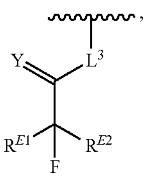
(i-14)
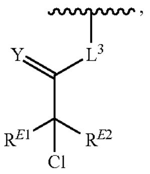

-continued
(i-15)
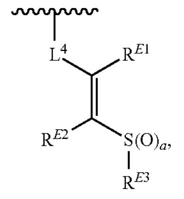
(i-16)
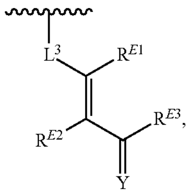
(i-17)
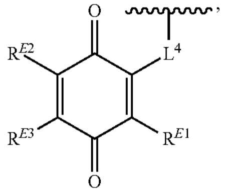
(i-18)
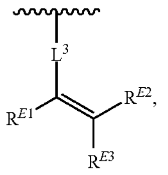
(i-19)
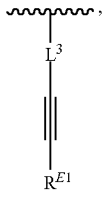
(i-20)
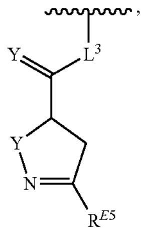
(i-21)
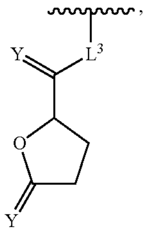
-continued
(i-22)
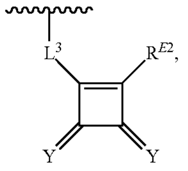
(i-23)
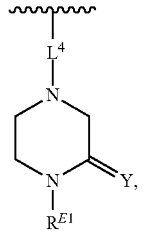
(i-24)
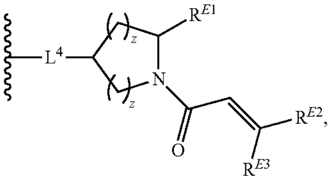
(i-25)
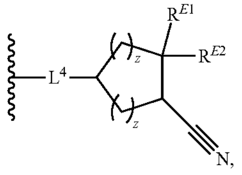
(i-26)
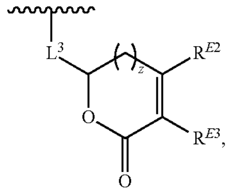
(i-27)
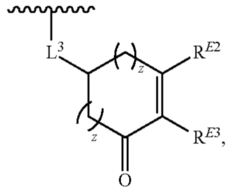
(i-28)
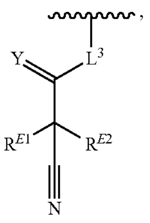
(i-29)
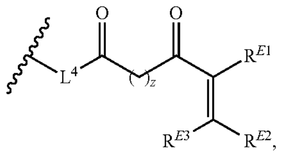

-continued (i-30)

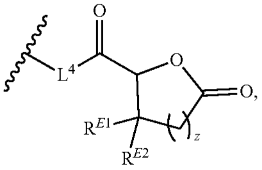

(i-31)

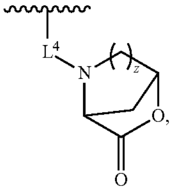

(i-32)

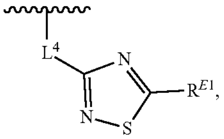

(i-33)

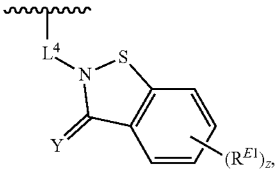

(i-34)

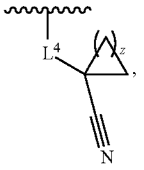

(i-35)

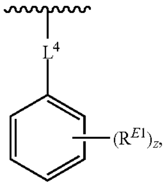

(i-36)

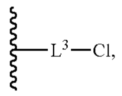

(i-37)

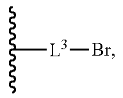

(i-38)

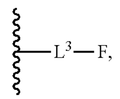

(i-39)

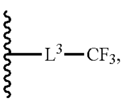

-continued (i-40)

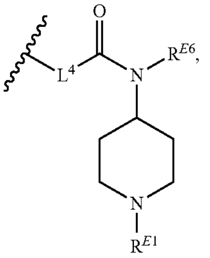

and (i-41)

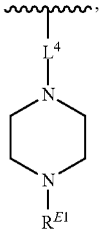

wherein, indicates the position of attachment to the compound of Formula (I);

$L^3$ is a bond or an $C_{1-4}$ hydrocarbon chain, optionally wherein one or more carbon units of the hydrocarbon chain are independently replaced with —C═O—, —O—, —S—, —$NR^{L3a}NR^{L3a}$C(═O)—, —C(═O)$NR^{L3a}$—, —SC(═O)—, —C(═O)S—, —OC(═O)—, —C(═O)O—, —$NR^{L3a}$C(═S)—, —C(═S)$NR^{L3a}$—, trans-$CR^{L3b}$═$CR^{L3b}$—, cis-$CR^{L3b}$═$CR^{L3b}$—, —C≡C—, —S(═O)—, —S(═O)O—, —OS(═O)—, —S(═O)$NR^{L3a}$—, —$NR^{L3a}$S(═O)—, —$S(═O)_2$—, —$S(═O)_2O$—, —$OS(═O)_2$—, —$S(═O)_2NR^{L3a}$—, or —$NR^{L3a}S(═O)_2$—, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, alkyl, alkenyl, alkynyl, carbocyclyl, heterocyclyl, aryl, or heteroaryl, or two $R^{L3b}$ groups are joined to form an carbocyclic or heterocyclic ring;

$L^4$ is a bond or alkyl;

each of $R^{E1}$, $R^{E2}$, and $R^{E3}$ is independently hydrogen, halogen, amido, carboxy, alkyl, alkenyl, alkynyl, carbocyclyl, heterocyclyl, aryl, heteroaryl, —CN, —$CH_2OR^{EE}$, —$CH_2N(R^{EE})_2$, —$CH_2SR^{EE}$, —$OR^{EE}$, —$N(R^{EE})_2$, —$Si(R^{EE})_3$, or —$SR^{EE}$, wherein each instance of $R^{EE}$ is independently hydrogen, alkyl, alkoxy, alkenyl, alkynyl, carbocyclyl, heterocyclyl, aryl, or heteroaryl, or two $R^{EE}$ groups are joined to form an heterocyclic ring; or $R^{E1}$ and $R^{E3}$, or $R^{E2}$ and $R^{E3}$, or $R^{E1}$ and $R^{E2}$ are joined to form an carbocyclic or heterocyclic ring;

$R^{4E}$ is a leaving group or alkyl;

$R^{E5}$ is halogen;

$R^{E6}$ is hydrogen, substituted or unsubstituted $C_{1-6}$ alkyl, or a nitrogen protecting group; each instance of Y is independently O, S, or $NR^{E7}$, wherein $R^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits; and each instance of $R^{E8}$, if present, is independently selected from hydrogen, halogen, acyl, alkyl, alkenyl, alkynyl, carbocyclyl, heterocyclyl, aryl, heteroaryl, $—OR^{D1}$, $—N(R^{D1a})_2$, and $—SR^{D1}$, wherein each occurrence of $R^{D1}$ is independently selected from hydrogen, acyl, alkyl, alkenyl, alkynyl, carbocyclyl, heterocyclyl, aryl, heteroaryl, an oxygen protecting group when attached to an oxygen atom, and a sulfur protecting group when attached to a sulfur atom;

wherein each occurrence of $R^{D1a}$ is independently selected from hydrogen, acyl, alkyl, alkenyl, alkynyl, carbocyclyl, heterocyclyl, aryl, heteroaryl, and a nitrogen protecting group, or optionally two instances of $R^{D1a}$ are taken together with their intervening atoms to form a substituted or unsubstituted heterocyclic or substituted or unsubstituted heteroaryl ring; or two $R^{E8}$ groups are joined to form an carbocyclyl, heterocyclyl, aryl, or heteroaryl ring.

In certain embodiments, the electrophile has structure represented by any one of the following formula:

(i-1)

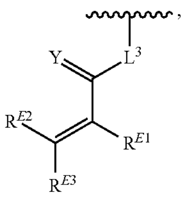

(i-2)

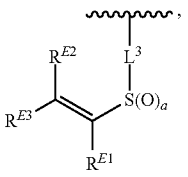

(i-3)

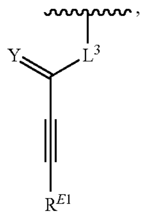

(i-4)

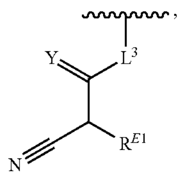

(i-5)

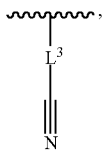

-continued (i-6)

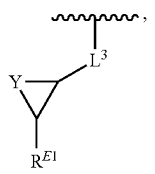

(i-7)

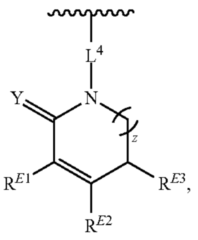

(i-8)

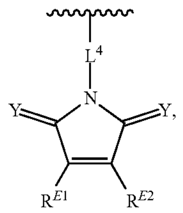

(i-9)

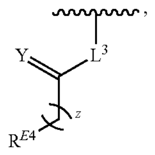

(i-10)

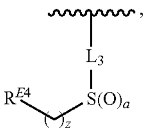

(i-11)

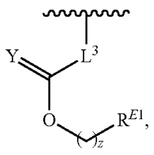

(i-12)

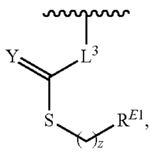

(i-13)

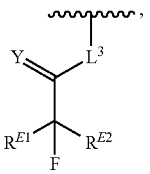

-continued
(i-14)
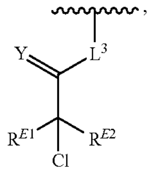
(i-15)
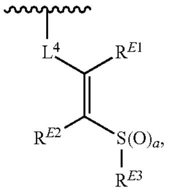
(i-16)
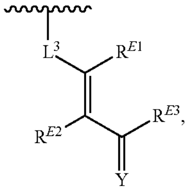
(i-17)
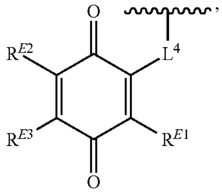
(i-18)
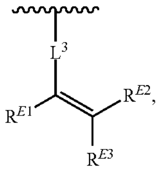
(i-19)
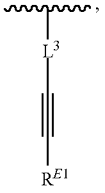
(i-20)
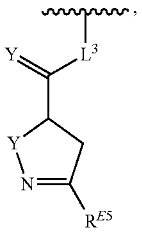
-continued
(i-21)
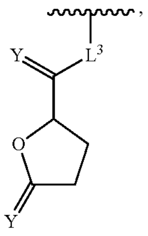
(i-22)
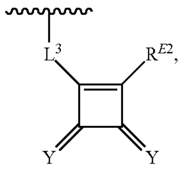
(i-23)
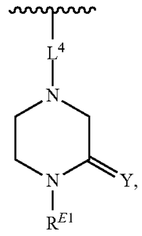
(i-24)
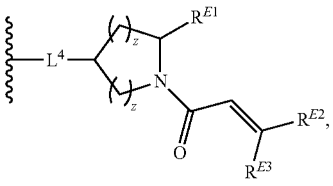
(i-25)
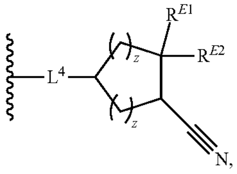
(i-26)
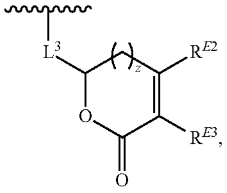
(i-27)
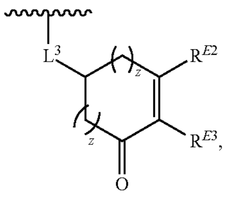

-continued (i-28)

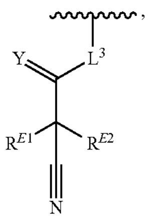

(i-29)

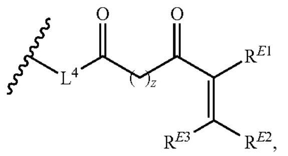

(i-30)

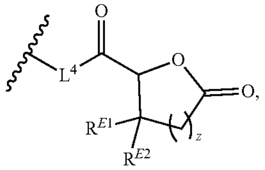

(i-31)

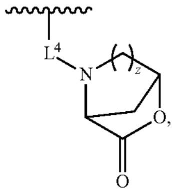

(i-32)

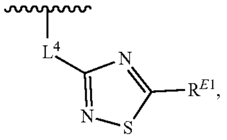

(i-33)

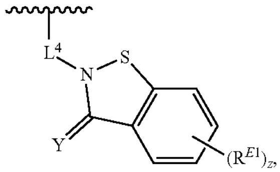

(i-34)

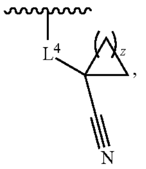

(i-35)

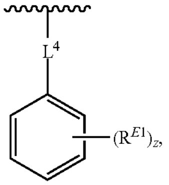

(i-36)

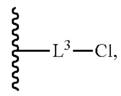

-continued (i-37)

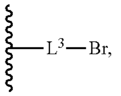

(i-38)

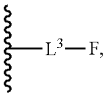

(i-39)

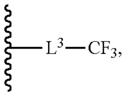

(i-40)

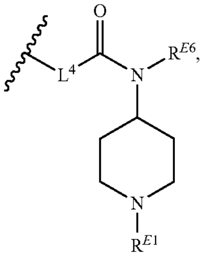

and (i-41)

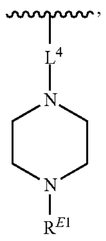

wherein,

⌇ indicates the position of attachment to the compound of Formula (I);

$L^3$ is a bond or an $C_{1-4}$ hydrocarbon chain, optionally wherein one or more carbon units of the hydrocarbon chain are independently replaced with —C(═O)—, —O—, —S—, —$NR^{L3a}NR^{L3a}$C(═O)—, —C(═O)$NR^{L3a}$—, —SC(═O)—, —C(═O)S—, —OC(═O)—, —C(═O)O—, —$NR^{L3a}$C(═S)—, —C(═S)$NR^{L3a}$—, trans-$CR^{L3b}$═$CR^{L3b}$—, cis-$CR^{L3b}$═$CR^{L3b}$—, —C≡C—, —S(═O)—, —S(═O)O—, —OS(═O)—, —S(═O)$NR^{L3a}$—, —$NR^{L3a}$S(═O)—, —$S(═O)_2$—, —$S(═O)_2O$—, —$OS(═O)_2$—, —$S(═O)_2NR^{L3a}$—, or —$NR^{L3a}S(═O)_2$—, wherein $R^{L3a}$ is hydrogen, substituted or unsubstituted $C_{1-6}$ alkyl, or a nitrogen protecting group, and wherein each occurrence of $R^{L3b}$ is independently hydrogen, halogen, alkyl, alkenyl, alkynyl, carbocyclyl, heterocyclyl, aryl, or heteroaryl, or two $R^{L3b}$ groups are joined to form an carbocyclic or heterocyclic ring;

$L^4$ is a bond or an optionally substituted, branched or unbranched $C_{1-6}$ hydrocarbon chain;

each of $R^{E1}$, $R^{E2}$, and $R^{E3}$ is independently hydrogen, halogen, alkyl, alkenyl, alkynyl, carbocyclyl, heterocyclyl, aryl, heteroaryl, —CN, —$CH_2OR^{EE}$, —$CH_2N(R^{EE})_2$, —$CH_2SR^{EE}$, —$OR^{EE}$, —$N(R^{EE})_2$, —$Si(R^{EE})_3$, or —$SR^{EE}$, wherein each instance of $R^{EE}$ is independently hydrogen, alkyl, alkoxy, alkenyl, alkynyl, carbocyclyl, heterocyclyl, aryl, or heteroaryl, or two $R^{EE}$ groups are joined to form an heterocyclic ring; or $R^{E1}$ and $R^{E3}$, or $R^{E2}$ and $R^{E3}$, or $R^{E1}$ and $R^{E2}$ are joined to form an carbocyclic or heterocyclic ring;

$R^{4E}$ is a leaving group or alkyl;

$R^{E5}$ is halogen;

$R^{E6}$ is hydrogen, substituted or unsubstituted $C_{1-6}$ alkyl, or a nitrogen protecting group;

each instance of Y is independently O, S, or $NR^{E7}$, wherein $R^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits; and each instance of $R^{E8}$, if present, is independently selected from hydrogen, halogen, acyl, alkyl, alkenyl, alkynyl, carbocyclyl, heterocyclyl, aryl, heteroaryl, $—OR^{D1}$, $—N(R^{D1a})_2$, and $—SR^{D1}$, wherein each occurrence of $R^{D1}$ is independently selected from hydrogen, acyl, alkyl, alkenyl, alkynyl, carbocyclyl, heterocyclyl, aryl, heteroaryl, an oxygen protecting group when attached to an oxygen atom, and a sulfur protecting group when attached to a sulfur atom;

wherein each occurrence of $R^{D1a}$ is independently selected from hydrogen, acyl, alkyl, alkenyl, alkynyl, carbocyclyl, heterocyclyl, aryl, heteroaryl, and a nitrogen protecting group, or optionally two instances of $R^{D1a}$ are taken together with their intervening atoms to form a substituted or unsubstituted heterocyclic or substituted or unsubstituted heteroaryl ring; or two $R^{E8}$ groups are joined to form an carbocyclyl, heterocyclyl, aryl, or heteroaryl ring.

In certain preferred embodiments, the electrophile has a structure represented by Formula i-1:

(i-1)

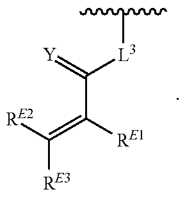

In certain embodiments, $L^3$ is a bond.

In certain embodiments, $R^{E1}$, $R^{E2}$, and $R^{E3}$ are each hydrogen. In other embodiments, $R^{E1}$ and $R^{E2}$ are each hydrogen; and $R^{E3}$ is amido or alkyl (e.g., aminoalkyl, such as dimethylaminoalkyl). In certain embodiments, $R^{E1}$ and $R^{E2}$ are each hydrogen; and $R^{E3}$ is dimethylaminoalkyl. In certain embodiments, $R^{E1}$ and $R^{E2}$ are each hydrogen; and $R^{E3}$ is carboxy.

In certain embodiments, $R^{E1}$ and $R^{E3}$ are in the cis configuration. In other embodiments, $R^{E1}$ and $R^{E3}$ are in the trans configuration.

In certain embodiments, Y is O.

In other preferred embodiments, the electrophile has a structure represented by Formula i-2:

(i-2)

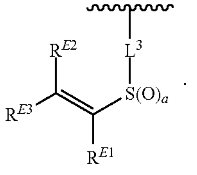

In certain embodiments, $L^3$ is a bond.

In certain embodiments, a is 2.

In certain embodiments, $R^{E1}$, $R^{E2}$, and $R^{E3}$ are each hydrogen.

In yet other preferred embodiments, the electrophile has a structure represented by Formula i-3:

(i-3)

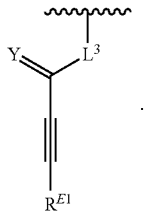

In certain embodiments, $L^3$ is a bond.

In certain embodiments, $R^{E1}$ is hydrogen.

In yet other preferred embodiments, the electrophile has a structure represented by Formula i-9:

(i-9)

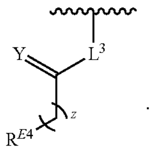

In certain embodiments, $L^3$ is a bond.

In certain embodiments, Y is O.

In certain embodiments, z is 1. In other embodiments, Z is 2.

In certain embodiments, $R^{E4}$ is alkyl (e.g., methyl). In other embodiments, $R^{4E}$ is halo (e.g., chloro).

In yet other preferred embodiments, the electrophile has a structure represented by Formula i-13:

(i-13)

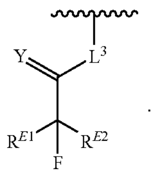

In certain embodiments, $L^3$ is a bond.

In certain embodiments, Y is O.

In certain embodiments, $R^{E1}$ is hydrogen.

In certain embodiments, $R^{4E}$ is halo (e.g., chloro).

In certain embodiments, A is aryl (e.g., phenyl or naphthyl). In other embodiments, A is heteroaryl (e.g., pyridonyl or thiophenyl).

In certain embodiments, $X^1$ is O.

In certain embodiments, $R^{1B}$ is H.

In certain embodiments, $R^{2A}$ is H.

In certain embodiments, $R^{2B}$ is H.

In certain embodiments, the compound has a structure represented by Formula II or III:

II

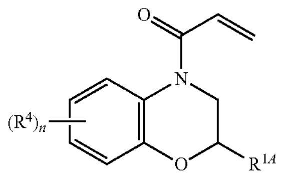

III

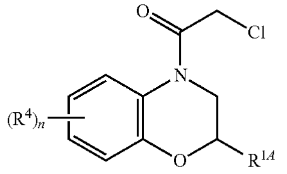

or a pharmaceutically acceptable salt thereof.

In certain embodiments, the compound has a structure represented by Formula II:

II

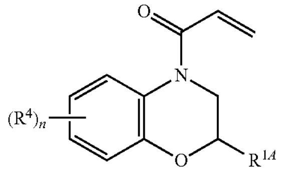

or a pharmaceutically acceptable salt thereof.

In certain embodiments, the compound has a structure represented by Formula IIa or IIb:

IIa

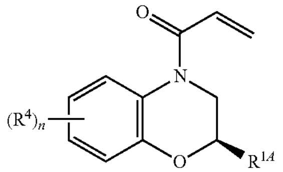

IIb

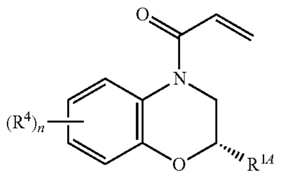

or a pharmaceutically acceptable salt thereof.

In certain embodiments, the compound has a structure represented by Formula III:

III

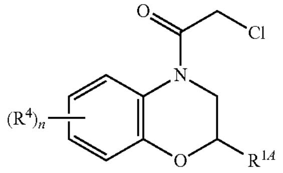

or a pharmaceutically acceptable salt thereof.

In certain embodiments, the compound has a structure represented by Formula IIIa or IIIb:

IIIa

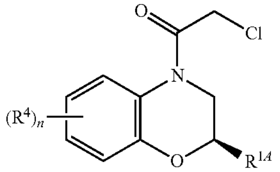

IIIb

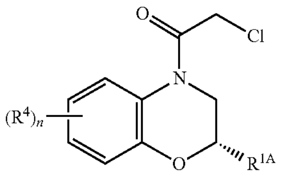

or a pharmaceutically acceptable salt thereof.

In certain embodiments, $R^{1A}$ is amide. In other embodiments, $R^{1A}$ is ester (e.g., ethyl ester). In yet other embodiments, $R^{1A}$ is carboxyl. In yet other embodiments, $R^{1A}$ is alkyl (e.g., ethyl or propyl). In yet other embodiments, $R^{1A}$ is aryl (e.g., phenyl). In yet other embodiments, $R^{1A}$ is heteroaryl (e.g., pyridyl, triazolyl, or imidazolyl). In yet other embodiments, $R^{1A}$ is heterocyclyl (e.g., imidazolidinyl, such as methylimidazolidinyl, or pyrrolidinyl). In yet other embodiments, $R^{1A}$ is aralkyl (e.g., benzyl). In yet other embodiments, $R^{1A}$ is heteroaralkyl (e.g., pyridylmethyl). In yet other embodiments, $R^{1A}$ is carbamate. In yet other embodiments, $R^{1A}$ is urea. In yet other embodiments, $R^{1A}$ is $R^{1A}$ is cycloalkyloxy (e.g., cyclopentyloxy), aryloxy (e.g., phenoxy), heteroaryloxy (e.g., pyridyloxy). In certain embodiments, $R^{1A}$ is substituted with alkyl (e.g., methyl or ethyl), cycloalkyl (e.g., cyclopentyl), heteroaryl (e.g., pyridyl), acyl (e.g., acetyl), heteroaryl (e.g., pyridyl), halo (e.g., chloro), hydroxyl, alkyloxy (e.g., methyloxy), amino, alkylamino (e.g., methylamino or dimethylamino), heterocyclyl (e.g., pyrrolidinyl), phosphino (e.g., dimethylphosphine oxide), phosphonyl (e.g., phosphonic acid), carboxyl, sulfonyl (e.g., methylsulfonyl), or sulfonamido. In other embodiments, $R^{1A}$ and $R^{1B}$ combine to form cycloalkyl (e.g., cylcopentyl) or heterocyclyl (e.g., pyrrolidinyl, pyrrolidonyl, tetrahydrothiophenyl, such as tetrahydrothiophenedioxide). In certain embodiments, $R^{1A}$ and $R^{1B}$ combine to form cycloalkyl (e.g., cylcopentyl) or heterocyclyl (e.g., pyrrolidinyl, pyrrolidonyl, tetrahydrothiophenyl, such as tetrahydrothiophenedioxide) and the resultant cycloalkyl or heterocyclyl is substituted with alkyl (e.g., methyl or ethyl), cycloalkyl (e.g., cyclopentyl), heteroaryl (e.g., pyridyl), acyl (e.g., acetyl), heteroaryl (e.g., pyridyl), halo (e.g., chloro), hydroxyl, alkyloxy (e.g., methyloxy), amino, alkylamino (e.g., methylamino or dimethylamino), heterocyclyl (e.g., pyrrolidinyl), phosphino (e.g., dimethylphosphine oxide), phosphonyl (e.g., phosphonic acid), carboxyl, sulfonyl (e.g., methylsulfonyl), or sulfonamido.

In certain embodiments, the compound has a structure represented by Formula IV or V:

IV

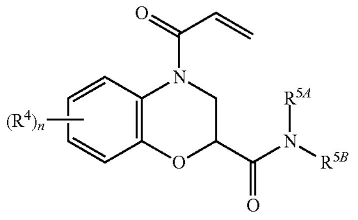

V

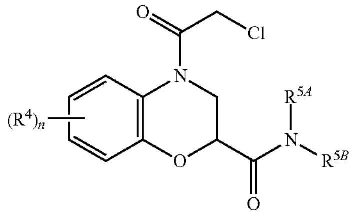

or a pharmaceutically acceptable salt thereof, wherein $R^{5A}$ and $R^{5B}$ are each independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

In certain embodiments, the compound has a structure represented by Formula IV:

IV

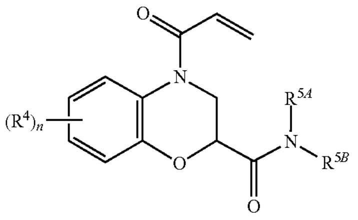

or a pharmaceutically acceptable salt thereof, wherein $R^{5A}$ and $R^{5B}$ are each independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

In certain embodiments, the compound has a structure represented by Formula IVa:

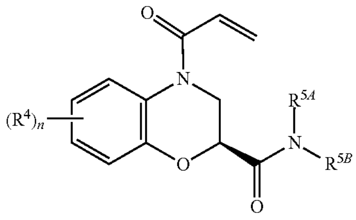

or a pharmaceutically acceptable salt thereof, wherein $R^{5A}$ and $R^{5B}$ are each independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

In certain embodiments, the compound has a structure represented by Formula IVb:

IVa

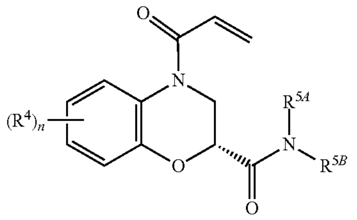

or a pharmaceutically acceptable salt thereof, wherein $R^{5A}$ and $R^{5B}$ are each independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

In certain embodiments, the compound has a structure represented by Formula V:

V

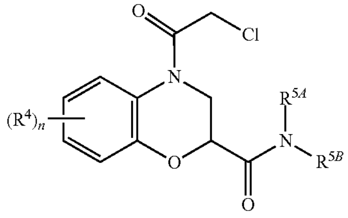

or a pharmaceutically acceptable salt thereof, wherein $R^{5A}$ and $R^{5B}$ are each independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

In certain embodiments, the compound has a structure represented by Formula IIIa:

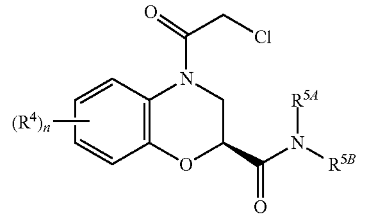

Va or a pharmaceutically acceptable salt thereof, wherein $R^{5A}$ and $R^{5B}$ are each independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

In certain embodiments, the compound has a structure represented by Formula IIIb:

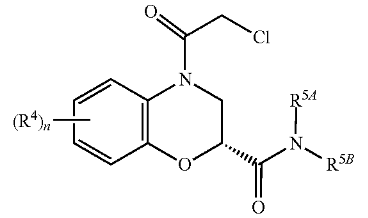

Vb or a pharmaceutically acceptable salt thereof, wherein $R^{5A}$ and $R^{5B}$ are each independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

In certain embodiments, $R^{5A}$ is H. In other embodiments, $R^{5A}$ is alkyl (e.g., methyl).

In certain embodiments, $R^{5B}$ is H. In other embodiments, $R^{5B}$ is alkyl (e.g., methyl). In yet other embodiments, $R^{5B}$ is heteroaralkyl (e.g., pyrazolealkyl, such as N-methylpyrazolealkyl). In yet other embodiments, $R^{5B}$ is cycloalkyl (e.g., cyclohexyl). In yet other embodiments, $R^{5B}$ is cycloalkylalkyl (e.g., cyclopropylalkyl). In yet other embodiments, $R^{5B}$ is aryl (e.g., phenyl). In yet other embodiments, $R^{5B}$ is heteroaryl (e.g., trioazole, such as N-methyltriazole).

In certain embodiments, $R^{5B}$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, cycloalkyl, cycloalkylalkyl, heterocyclylalkyl, heteroaralkyl, sulfonamide, aryl, heteroaryl, heterocyclyl, or aralkyl.

In certain preferred embodiments, n is 1.

In certain embodiments, $R^4$ is ester (e.g., methyl ester), halo (e.g., bromo), sulfonamide (e.g., dimethyl sulfonamide), alkyl (e.g., methyl), or aryl (e.g., phenyl). In certain embodiments, $R^4$ is heteroaryl (e.g., pyrazolyl, such as N-methylpyrazolyl, or pyrimidinyl).

In certain embodiments, the compound is selected from

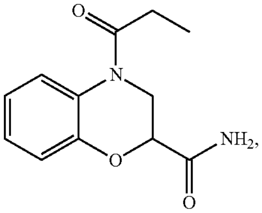

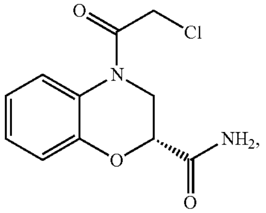

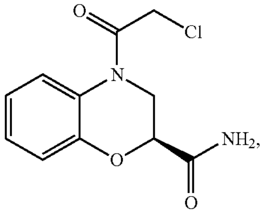

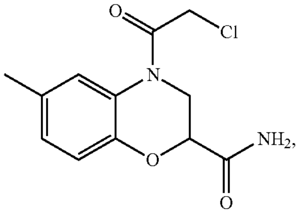

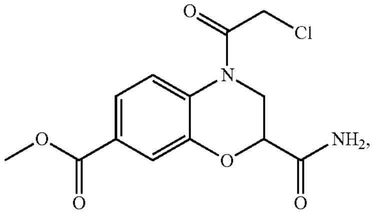

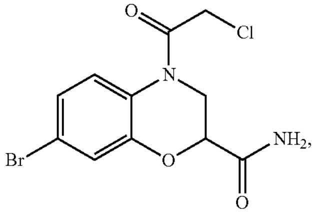

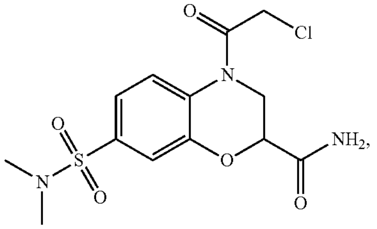

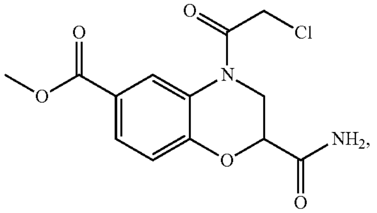

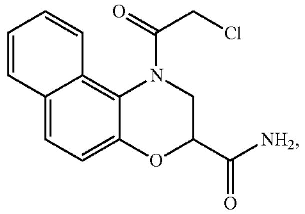

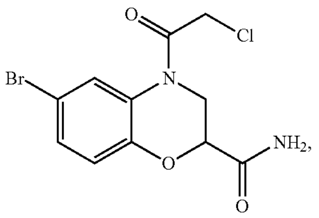

-continued
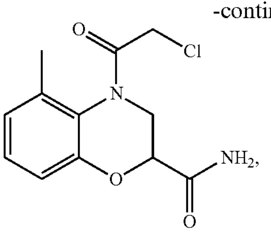
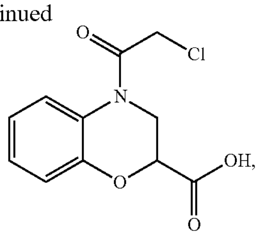
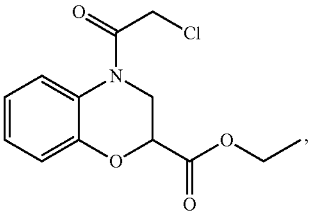
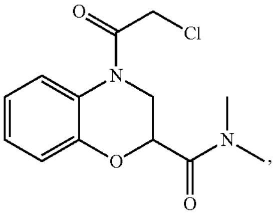
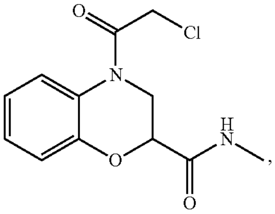
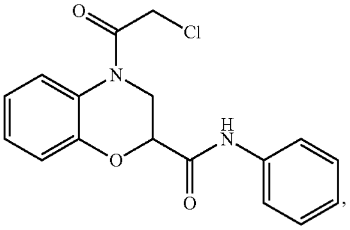
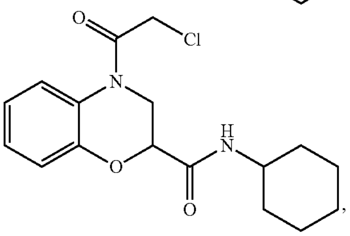
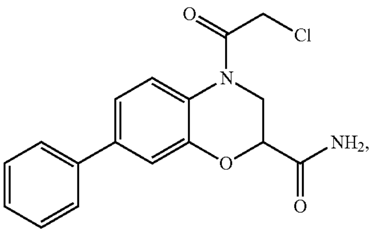
-continued
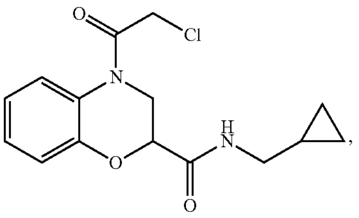
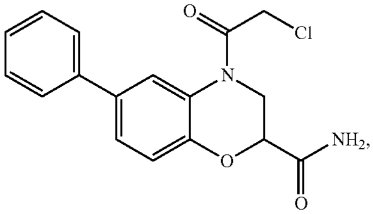
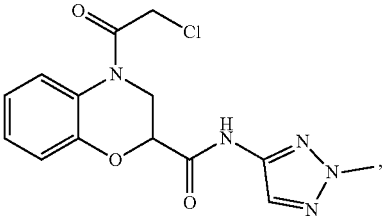
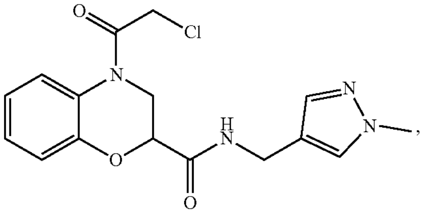
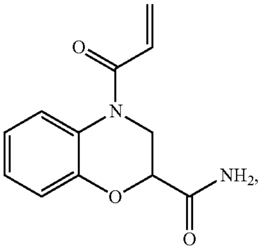
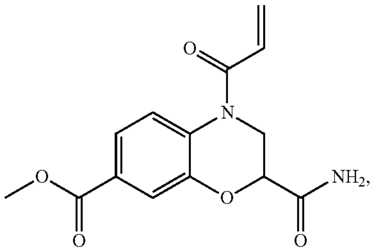
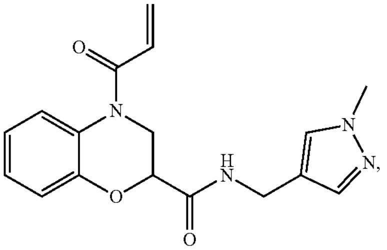

-continued
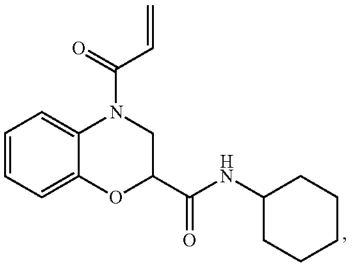
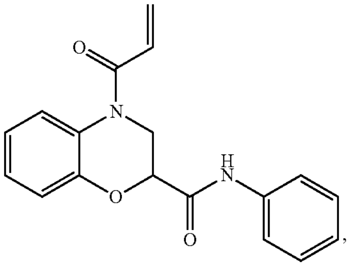
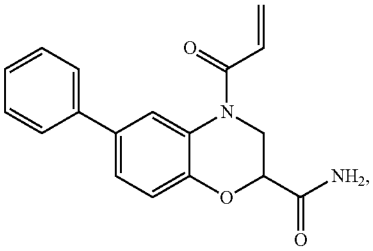
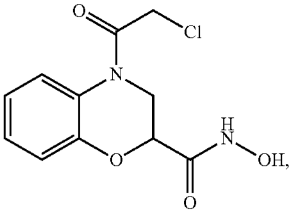
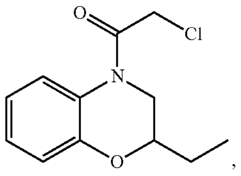
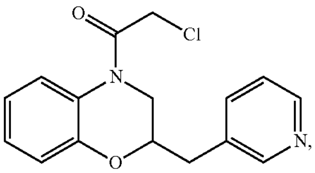
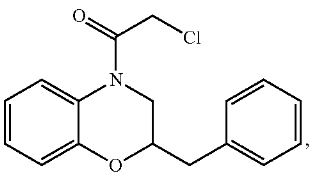
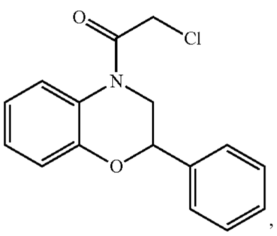
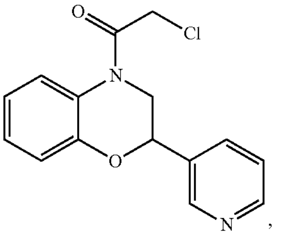
-continued
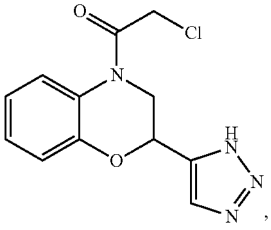
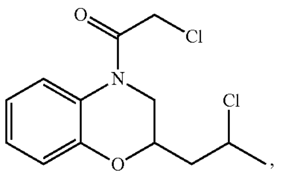
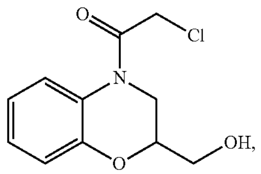
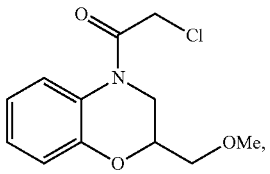
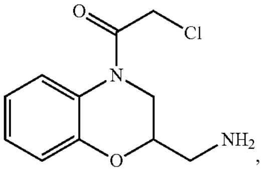
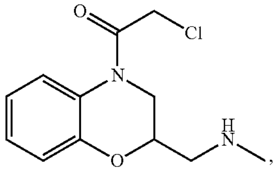
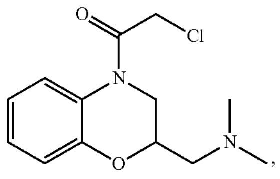
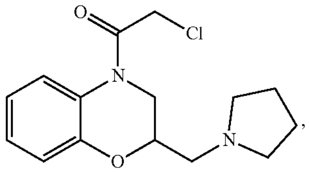
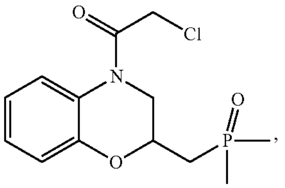
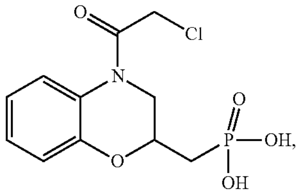
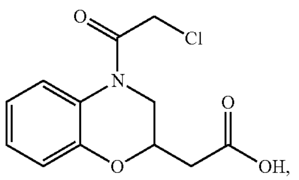
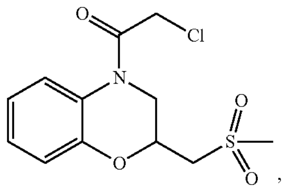
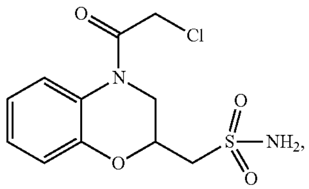

-continued
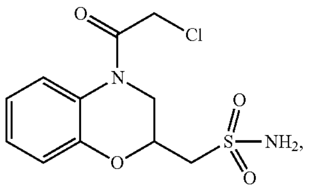
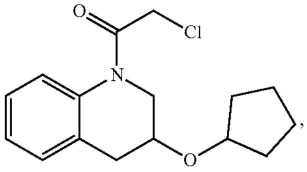
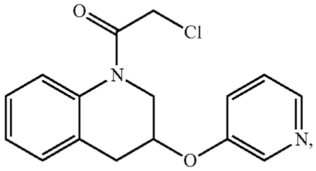
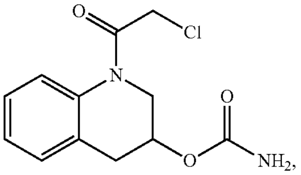
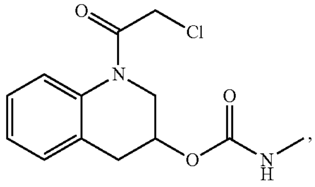
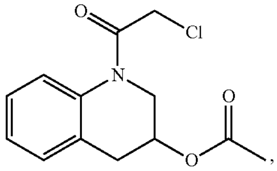
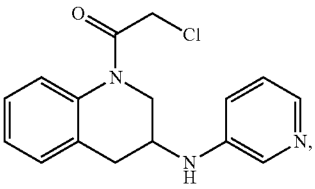
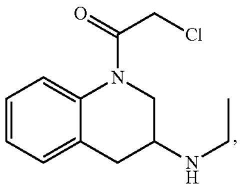
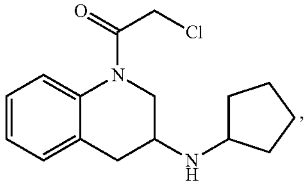
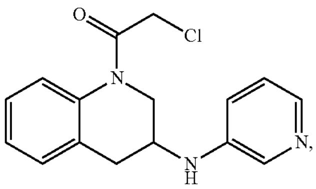
-continued
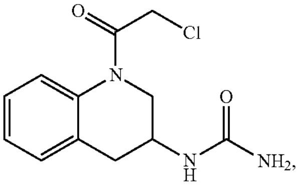
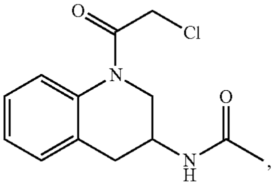
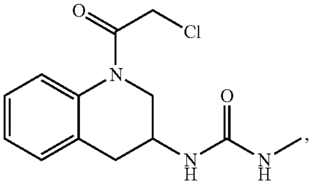
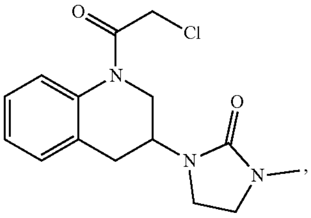
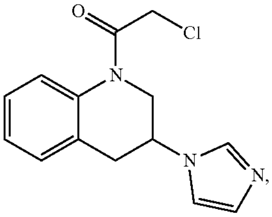
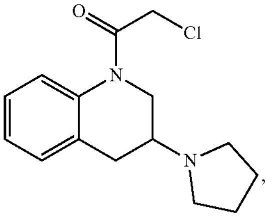
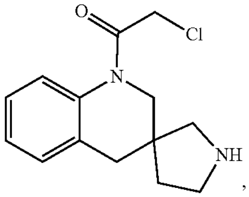
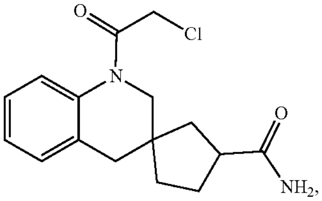
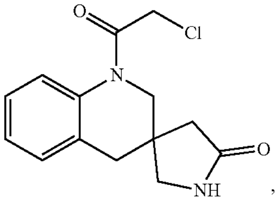
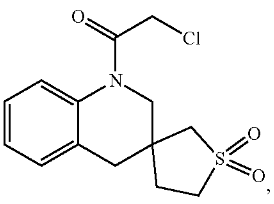
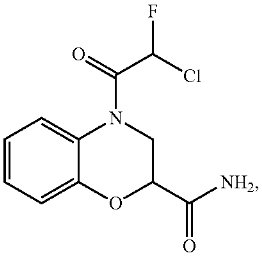
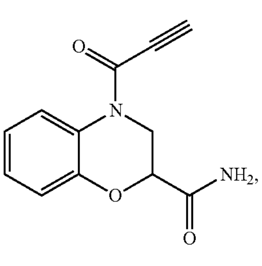

-continued

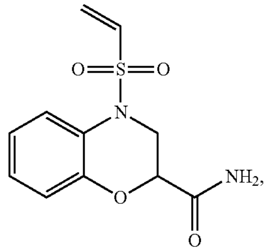

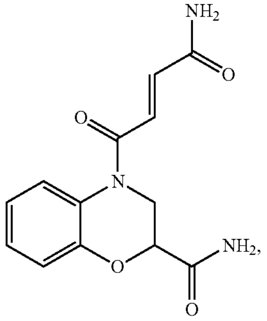

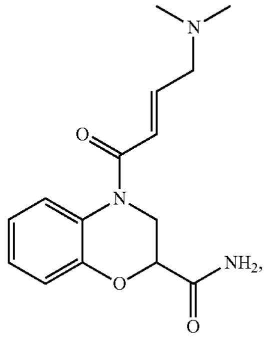

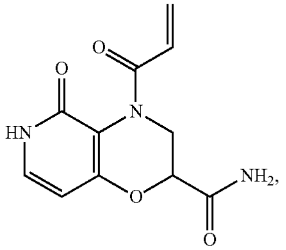

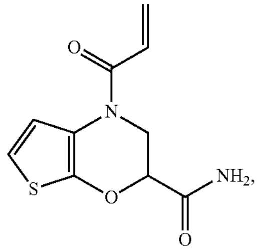

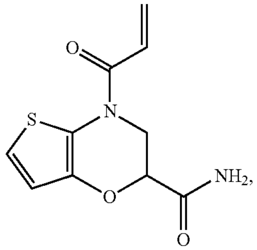

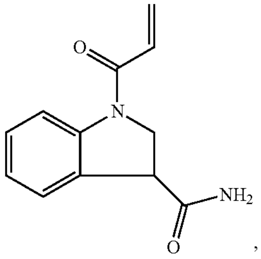

,

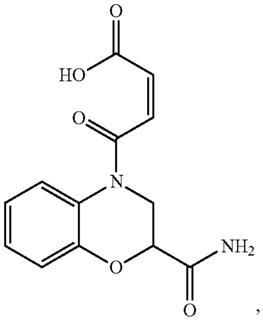

,

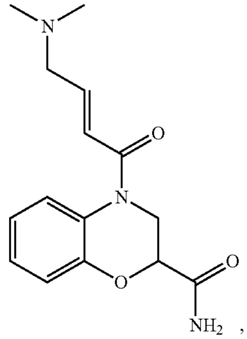

,

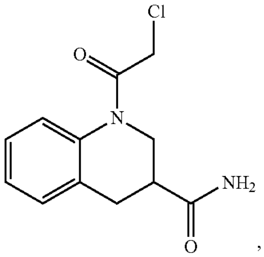

,

-continued

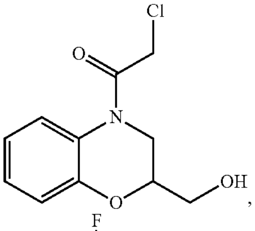

,

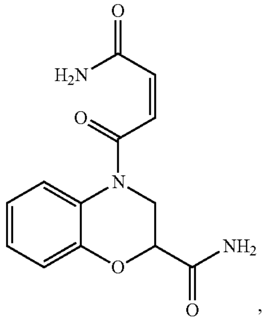

,

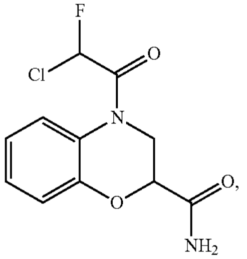

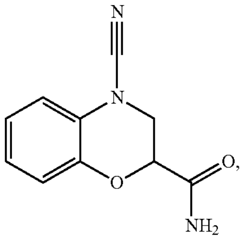

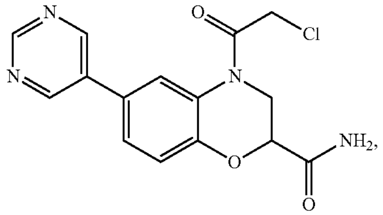

and

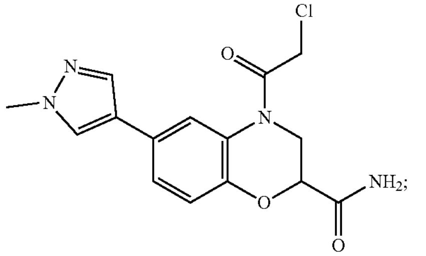

or a pharmaceutically acceptable salt thereof.

In another aspect, the present disclosure provides pharmaceutical compositions comprising a compound of the disclosure and a pharmaceutically acceptable excipient.

In yet another aspect, the present disclosure provides methods of treating cancer in a subject in need therefore, comprising administering a compound of the disclosure or a pharmaceutically acceptable salt thereof to the subject.

In yet another aspect, the present disclosure provides methods of treating cancer by inhibiting creatine kinase in a subject in need therefore, comprising administering a compound of the disclosure or a pharmaceutically acceptable salt thereof to the subject. In certain embodiments, the creatine kinase is CK-MM, CK-BB, or CK-MB.

In certain preferred embodiments, the cancer is associated with creatine kinase overexpression. In certain embodiments, the cancer is liver cancer. In other embodiments, the cancer is pancreatic cancer. In yet other embodiments, the cancer is lung cancer. In yet other embodiments, the cancer is colon cancer. In yet other embodiments, the cancer is a hematological malignancy. In certain embodiments, the hematological malignancy is myelogenous leukemia, myeloid leukemia (e.g., acute myeloid leukemia), myelodysplastic syndrome, lymphoblastic leukemia (e.g., acute lymphoblastic leukemia), chronic lymphocytic leukemia (CLL), small lymphocytic lymphoma (SLL), high risk CLL, follicular lymphoma, diffuse large B-cell lymphoma (DLBCL) (e.g., DLBCL or ABC-DLBLC), mantle cell lymphoma (MCL), Waldenstrom's macroglobulinemia (WM), multiple myeloma, marginal zone lymphoma (MZL), Burkitt's lymphoma, non-Burkitt high grade B cell lymphoma, extranodal marginal zone B cell lymphoma, transformed high grade B-cell lymphoma (HGBL), lymphoplasmacytic lymphoma (LPL), central nervous system lymphoma (CNSL), or MALT lymphoma. In certain embodiments, the hematological malignancy is acute myeloid leukemia.

In yet another aspect, the present disclosure provides methods of inhibiting creatine kinase in a cell, comprising contacting the cell with a compound of the disclosure or a pharmaceutically acceptable salt thereof. In certain embodiments, the creatine kinase is CK-MM, CK-BB, or CK-MB.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term “alkylamino”, as used herein, refers to an amino group substituted with at least one alkyl group.

The term “alkylthio”, as used herein, refers to a thiol group substituted with an alkyl group and may be represented by the general formula alkylS—.

The term “amide”, as used herein, refers to a group

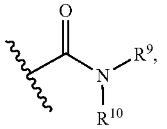

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms “amine” and “amino” are art-recognized and refer to both unsubstituted and substituted amines and salts thereof, e.g., a moiety that can be represented by

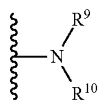
or
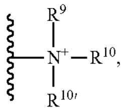

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term “aminoalkyl”, as used herein, refers to an alkyl group substituted with an amino group.

The term “aralkyl”, as used herein, refers to an alkyl group substituted with an aryl group.

The term “aryl” as used herein include substituted or unsubstituted single-ring aromatic groups in which each atom of the ring is carbon. Preferably the ring is a 5- to 7-membered ring, more preferably a 6-membered ring. The term “aryl” also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term “carbamate” is art-recognized and refers to a group

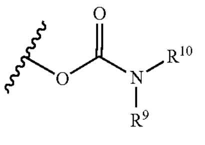
or
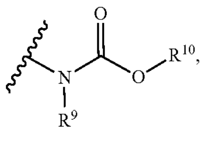

wherein $R^9$ and $R^{10}$ independently represent hydrogen or a hydrocarbyl group.

The term “carbocyclylalkyl”, as used herein, refers to an alkyl group substituted with a carbocycle group.

The term “carbocycle” includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term “fused carbocycle” refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary “carbocycles” include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. “Carbocycles” may be substituted at any one or more positions capable of bearing a hydrogen atom.

The term “carbocyclylalkyl”, as used herein, refers to an alkyl group substituted with a carbocycle group.

The term “carbonate” is art-recognized and refers to a group $—OCO_2—$.

The term “carboxy”, as used herein, refers to a group represented by the formula $—CO_2H$.

The term “cycloalkyl” includes substituted or unsubstituted non-aromatic single ring structures, preferably 4- to 8-membered rings, more preferably 4- to 6-membered rings. The term “cycloalkyl” also includes polycyclic ring systems having two or more cyclic rings in which two or more carbons are common to two adjoining rings wherein at least one of the rings is cycloalkyl and the substituent (e.g., $R^{100}$) is attached to the cycloalkyl ring, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, denzodioxane, tetrahydroquinoline, and the like.

The term “ester”, as used herein, refers to a group $—C(O)OR^9$ wherein $R^9$ represents a hydrocarbyl group.

The term “ether”, as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include “alkoxyalkyl” groups, which may be represented by the general formula alkyl-O-alkyl.

The terms “halo” and “halogen” as used herein means halogen and includes chloro, fluoro, bromo, and iodo.

The terms “hetaralkyl” and “heteroaralkyl”, as used herein, refers to an alkyl group substituted with a hetaryl group.

The terms “heteroaryl” and “hetaryl” include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms “heteroaryl” and “hetaryl” also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group $—OSO_3H$, or a pharmaceutically acceptable salt thereof.

The term "sulfonamide" is art-recognized and refers to the group represented by the general formulae

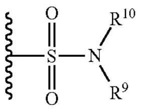

or

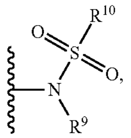

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group $SO_3H$, or a pharmaceutically acceptable salt thereof.

The term "sulfone" is art-recognized and refers to the group $—S(O)_2—$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $—C(O)SR^9$ or $—SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

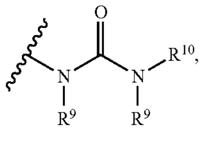

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds of the Disclosure

MYF-03-45-ester

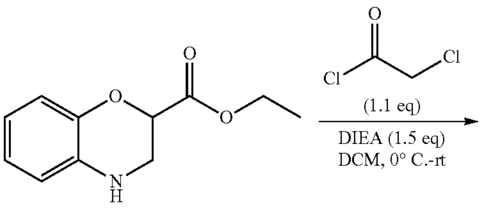

SM
CAS 22244-22-0

-continued

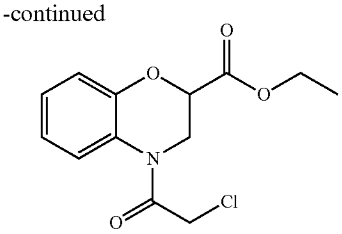

MYF-03-45-ester

Synthesis of ethyl 4-(2-chloroacetyl)-3,4-dihydro-2H-benzo[b][1,4]oxazine-2-carboxylate (Compound MYF-03-45-ester)

To ice cooled mixture of SM (1.0 eq) and DIEA (1.5 eq) in DCM was added 1M DCM solution of chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound MYF-03-45-ester as colorless oil. LC-MS (ESI) m/z: 284 $[M+1]^+$. $^1H$ NMR (500 MHz, DMSO-d6) δ 7.61 (br s, 1H), 7.21-7.09 (m, 1H), 7.02 (dd, J=8.2, 1.5 Hz, 1H), 6.98-6.92 (m, 1H), 5.22 (t, J=3.6 Hz, 1H), 4.82-4.24 (m, 3H), 4.12 (q, J=7.0 Hz, 2H), 3.78 (br s, 1H), 1.18 (t, J=7.1 Hz, 3H).

MYF-03-45-acid

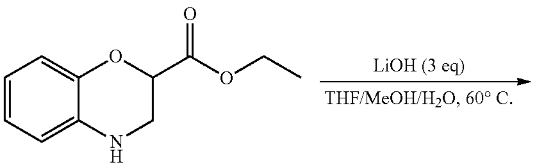

SM
CAS 22244-22-0

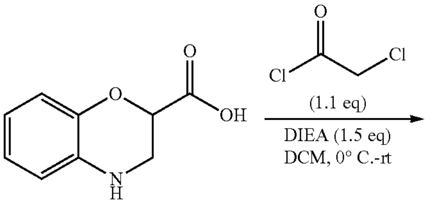

S1

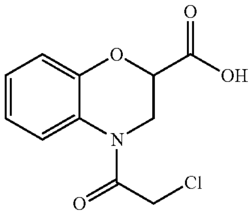

MYF-03-45-acid

Step 1: Synthesis of 3,4-dihydro-2H-benzo[b][1,4]oxazine-2-carboxylic acid

To a solution of SM (1.0 eq) in THF/MeOH/$H_2O$ (3:1:1) was added LiOH (3.0 eq). The resultant mixture was stirred and heated in 60° C. oil bath until hydrolysis was completed. The mixture was cooled to room temperature and pH was adjusted to 6-7 with 1M HCl. Then it was poured into water and extracted with DCM 3 times. After the combined organic phase was dried over anhydrous $Na_2SO_4$, it was concentrated and the residue was purified via prep-HPLC to afford 3,4-dihydro-2H-benzo[b][1,4]oxazine-2-carboxylic acid (S1) as colorless oil. LC-MS (ESI) m/z: 180 $[M+1]^+$.

Step 2: Synthesis of 4-(2-chloroacetyl)-3,4-dihydro-2H-benzo[b][1,4]oxazine-2-carboxylic acid (Compound MYF-03-45-acid)

To ice cooled mixture of intermediate obtained from step 1 (1.0 eq) and DIEA (1.5 eq) in DCM was added 1M DCM solution of chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound MYF-03-45-acid as colorless oil. LC-MS (ESI) m/z: 256 $[M+1]^+$. $^1H$ NMR (500 MHz, DMSO-d6) δ 7.81 (br s, 1H), 7.17-7.03 (m, 1H), 6.95 (d, J=8.1 Hz, 1H), 6.88 (t, J=7.7 Hz, 1H), 5.00-4.48 (m, 3H), 4.26 (d, J=12.8 Hz, 1H), 3.75 (br s, 1H).

MYF-03-45-II

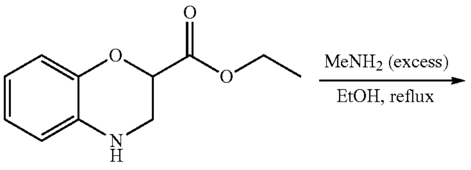

SM
CAS 22244-22-0

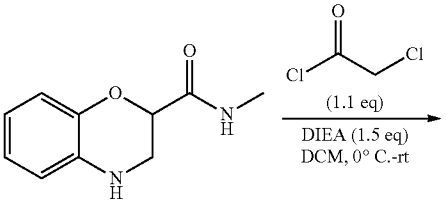

S2

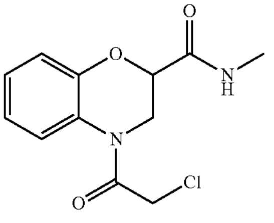

MYF-03-45-II

Step 1: Synthesis of N-methyl-3,4-dihydro-2H-benzo[b][1,4]oxazine-2-carboxamide

SM was dissolved in 33% wt methyl amine solution in EtOH and heated to reflux overnight. LC-MS indicated formation of desired amide product. The solution was concentrated and purified via silica gel flash chromatography to afford N-methyl-3,4-dihydro-2H-benzo[b][1,4]oxazine-2-carboxamide as light yellow gum. LC-MS (ESI) m/z: 193 $[M+1]^+$.

Step 2: Synthesis of 4-(2-chloroacetyl)-N-methyl-3,4-dihydro-2H-benzo[b][1,4]oxazine-2-carboxamide (Compound MYF-03-45-II)

To ice cooled mixture of intermediate obtained from step 1 (1.0 eq) and DIEA (1.5 eq) in DCM was added 1M DCM solution of chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound MYF-03-45-II as light yellow gum. LC-MS (ESI) m/z: 269 $[M+1]^+$. $^1H$ NMR (500 MHz, DMSO-d6) δ 8.16 (q, 1H), 7.74 (br s, 1H), 7.14 (t, J=7.9 Hz, 1H), 7.04 (dd, J=8.2, 1.5 Hz, 1H), 6.95 (ddd, J=8.4, 7.2, 1.5 Hz, 1H), 4.91 (br s, 1H), 4.72 (br s, 1H), 4.57 (d, J=13.9 Hz, 1H), 3.98 (br s, 2H), 2.62 (d, J=4.7 Hz, 3H).

MYF-03-84

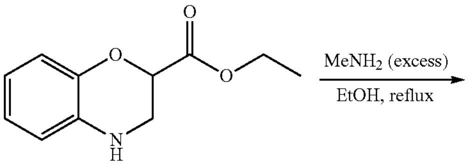

SM
CAS 22244-22-0

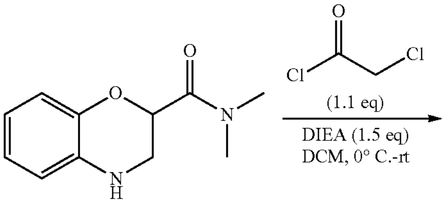

S3

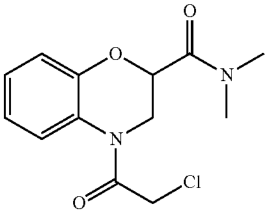

MYF-03-84

Step 1: Synthesis of N,N-dimethyl-3,4-dihydro-2H-benzo[b][1,4]oxazine-2-carboxamide SM and excess dimethyl amine were dissolved in EtOH and heated to reflux overnight. LC-MS indicated formation of desired amide product. The solution was concentrated and purified via silica gel flash chromatography to afford N,N-dimethyl-3,4-dihydro-2H-benzo[b][1,4]oxazine-2-carboxamide as light yellow gum. LC-MS (ESI) m/z: 207 $[M+1]^+$.

Step 2: Synthesis of 4-(2-chloroacetyl)-N,N-dimethyl-3,4-dihydro-2H-benzo[b][1,4]oxazine-2-carboxamide (Compound MYF-03-84)

To ice cooled mixture of intermediate obtained from step 1 (1.0 eq) and DIEA (1.5 eq) in DCM was added 1M DCM solution of chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound MYF-03-84 as light yellow gum. LC-MS (ESI) m/z: 283 $[M+1]^+$.

MYF-03-83

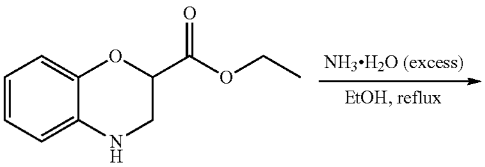

SM
CAS 22244-22-0

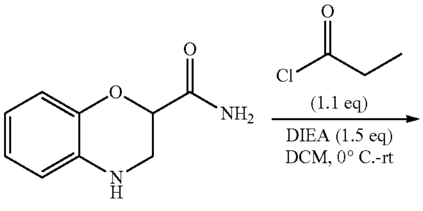

S4

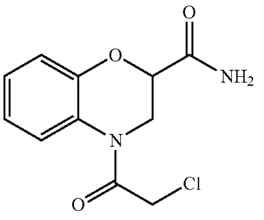

MYF-03-83

Step 1: Synthesis of 3,4-dihydro-2H-benzo[b][1,4]oxazine-2-carboxamide

SM and excess aqueous ammonia were dissolved in EtOH and heated to reflux overnight. LC-MS indicated formation of desired amide product. The solution was concentrated and purified via silica gel flash chromatography to afford 3,4-dihydro-2H-benzo[b][1,4]oxazine-2-carboxamide as light yellow gum. LC-MS (ESI) m/z: 179 $[M+1]^+$.

Step 2: Synthesis of 4-propionyl-3,4-dihydro-2H-benzo[b][1,4]oxazine-2-carboxamide (Compound MYF-03-83)

To ice cooled mixture of intermediate obtained from step 1 (1.0 eq) and DIEA (1.5 eq) in DCM was added 1M DCM solution of propionyl chloride (1.1 eq) dropwise, the mixture was stirred and allowed to warm to room temperature over 0.5 hour. LC-MS indicated formation of desired product. The mixture was concentrated and purified via prep-HPLC to afford compound MYF-03-83 as light yellow gum. LC-MS (ESI) m/z: 235 $[M+1]^+$.

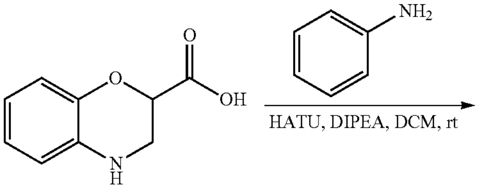

S1

-continued

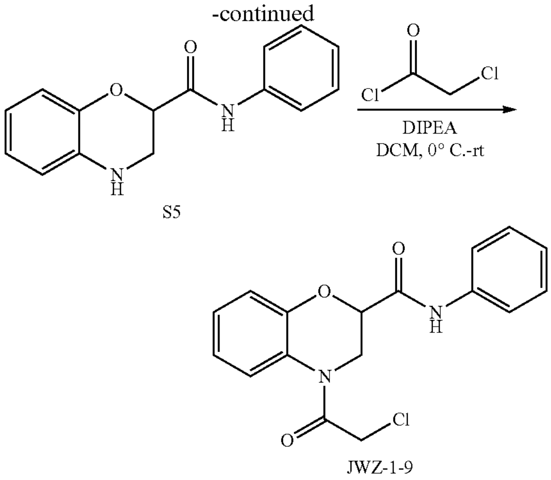

S5

JWZ-1-9

S5: To a mixture of S1 (90 mg, 0.5 mmol, 1.0 eq), HATU (0.5 mmol, 1.0 eq) in DCM (3 mL) was added DIPEA (1.5 mmol, 3.0 eq) and aniline (1 mmol, 2 eq) at room temperature. The mixture was stirred for 6 hours. The solution was concentrated and purified via silica gel flash chromatography to afford s5 (68 mg, 54%) as white solid LC-MS (ESI) m/z: 255 $[M+1]^+$.

JWZ-1-9: To ice cooled mixture of S5 (30 mg, 0.12 mmol) and DIPEA (1.5 eq) in DCM (1 mL) was added 1M DCM solution of 2-chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-9. (33 mg, 85%). LC-MS (ESI) m/z: 331 $[M+1]^+$. 1H NMR (500 MHz, DMSO-d6) δ 7.58 (d, J=8.0 Hz, 1H), 7.33 (t, J=7.9 Hz, 1H), 7.24 (s, 2H), 7.21-7.08 (m, 3H), 7.03 (s, 2H), 5.10 (d, J=4.4 Hz, 1H), 4.74-4.56 (m, 2H), 4.18-4.03 (m, 2H).

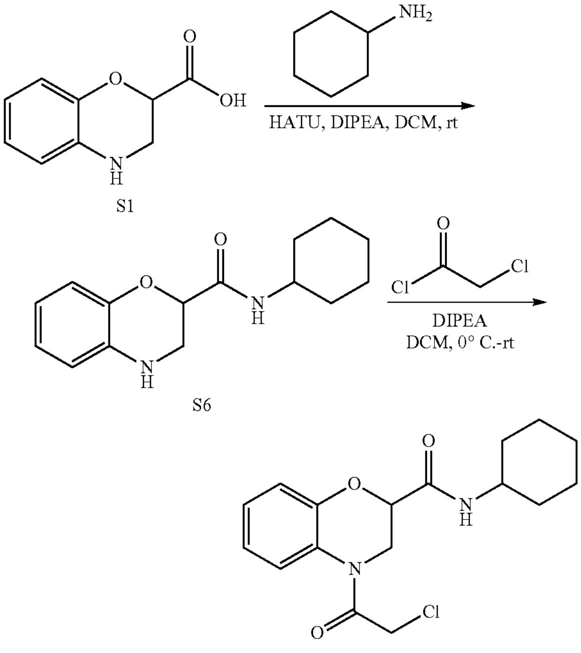

S1

S6

JWZ-1-11-1

S6: To a mixture of S1 (90 mg, 0.5 mmol, 1.0 eq), HATU (0.5 mmol, 1.0 eq) in DCM (3 mL) was added DIPEA (1.5 mmol, 3.0 eq) and cyclohexanamine (1 mmol, 2 eq) at room temperature. The mixture was stirred for 6 hours. The solution was concentrated and purified via silica gel flash chromatography to afford s6 (65 mg, 50%) as white solid LC-MS (ESI) m/z: 261 $[M+1]^+$.

JWZ-1-11-1: To ice cooled mixture of S5 (30 mg, 0.11 mmol) and DIPEA (1.5 eq) in DCM (1 mL) was added 1M DCM solution of 2-chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-11-1. (30 mg, 80%). LC-MS (ESI) m/z: 337 $[M+1]^+$. 1H NMR (500 MHz, DMSO-d6) δ 7.96 (d, J=8.1 Hz, 1H), 7.22-7.08 (m, 1H), 7.04 (dd, J=8.3, 1.5 Hz, 1H), 6.97-6.89 (m, 1H), 4.87 (s, 1H), 4.61 (d, J=11.6 Hz, 2H), 4.06 (dd, J=13.8, 5.4 Hz, 1H), 3.89 (dd, J=13.7, 3.3 Hz, 1H), 3.55 (dt, J=7.1, 3.4 Hz, 1H), 1.78-1.49 (m, 4H), 1.33-1.02 (m, 6H).

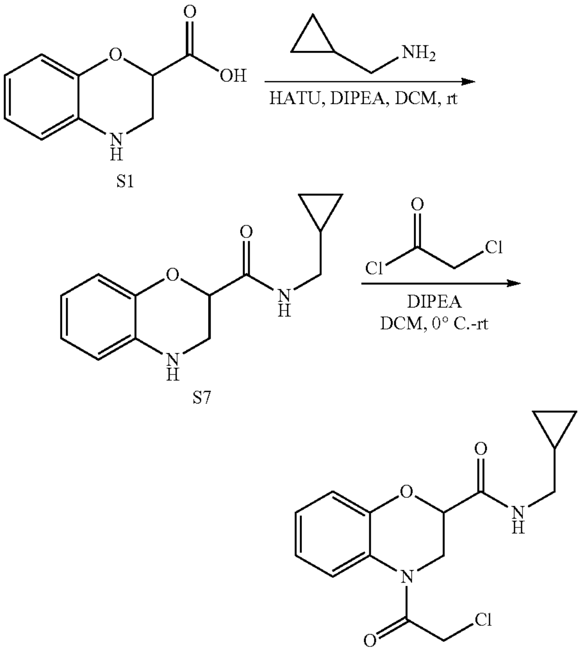

S1

S7

JWZ-1-14

S7: To a mixture of S1 (90 mg, 0.5 mmol, 1.0 eq), HATU (0.5 mmol, 1.0 eq) in DCM (3 mL) was added DIPEA (1.5 mmol, 3.0 eq) and cyclopropylmethanamine (1 mmol, 2 eq) at room temperature. The mixture was stirred for 6 hours. The solution was concentrated and purified via silica gel flash chromatography to afford s6 (52 mg, 45%) as white solid LC-MS (ESI) m/z: 233 $[M+1]^+$.

JWZ-1-14: To ice cooled mixture of S5 (30 mg, 0.13 mmol) and DIPEA (1.5 eq) in DCM (1 mL) was added 1M DCM solution of 2-chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-14. (32 mg, 81%). LC-MS (ESI) m/z: 309 $[M+1]^+$. 1H NMR (500 MHz, DMSO-d6) δ 8.28 (t, J=5.9 Hz, 1H), 7.14 (t, J=7.7 Hz, 1H), 7.05 (dd, J=8.2, 1.5 Hz, 1H), 6.99-6.88 (m, 1H), 4.92 (s, 1H), 4.69 (s, 1H), 4.58 (d, J=13.6 Hz, 1H), 3.97 (d, J=51.5 Hz, 2H), 3.02-2.91 (m, 2H), 1.01-0.75 (m, 1H), 0.46-0.25 (m, 2H), 0.13 (tt, J=4.7, 2.4 Hz, 2H).

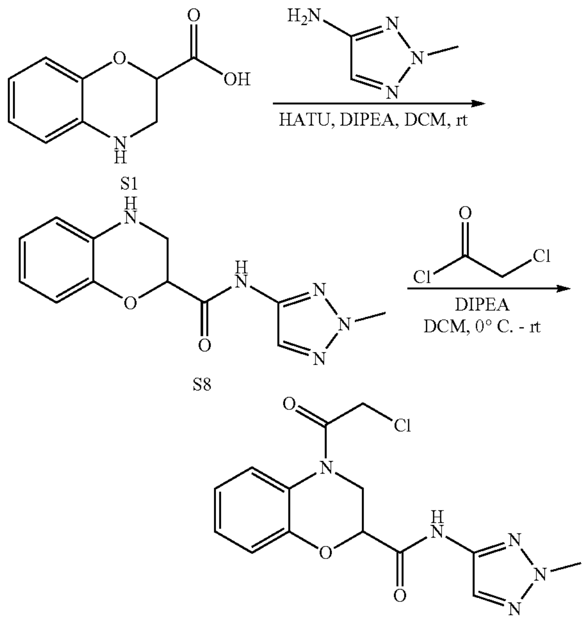

S1

S8

JWZ-1-17

S8: To a mixture of S1 (90 mg, 0.5 mmol, 1.0 eq), HATU (0.5 mmol, 1.0 eq) in DCM (3 mL) was added DIPEA (1.5 mmol, 3.0 eq) and 2-methyl-2H-1,2,3-triazol-4-amine (1 mmol, 2 eq) at room temperature. The mixture was stirred for 6 hours. The solution was concentrated and purified via silica gel flash chromatography to afford s6 (54 mg, 42%) as white solid LC-MS (ESI) m/z: 260 $[M+1]^+$.

JWZ-1-17: To ice cooled mixture of S5 (30 mg, 0.11 mmol) and DIPEA (1.5 eq) in DCM (1 mL) was added 1M DCM solution of 2-chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-14. (29 mg, 76%). LC-MS (ESI) m/z: 336 $[M+1]^+$. 1H NMR (500 MHz, DMSO-d6) δ 10.66 (s, 1H), 8.35 (s, 1H), 7.11 (dd, J=35.9, 8.5 Hz, 2H), 6.99-6.92 (m, 1H), 5.09 (s, 1H), 4.62 (d, J=13.0 Hz, 1H), 4.14-3.96 (m, 2H), 3.81 (s, 3H).

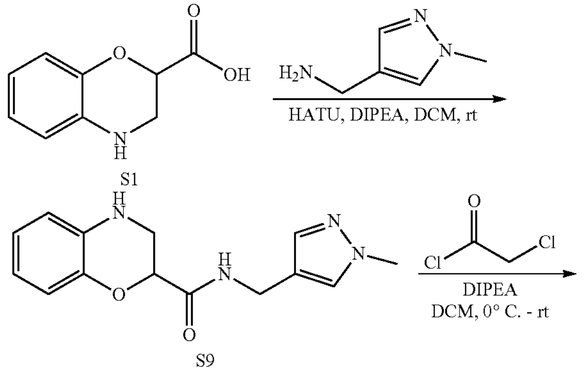

S1

S9

-continued

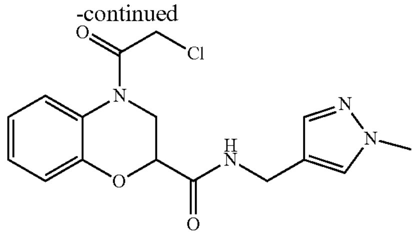

JWZ-1-24

S9: To a mixture of S1 (90 mg, 0.5 mmol, 1.0 eq), HATU (0.5 mmol, 1.0 eq) in DCM (3 mL) was added DIPEA (1.5 mmol, 3.0 eq) and 2-methyl-2H-1,2,3-triazol-4-amine (1 mmol, 2 eq) at room temperature. The mixture was stirred for 6 hours. The solution was concentrated and purified via silica gel flash chromatography to afford s6 (57 mg, 43%) as white solid LC-MS (ESI) m/z: 273 $[M+1]^+$.

JWZ-1-24: To ice cooled mixture of S5 (30 mg, 0.11 mmol) and DIPEA (1.5 eq) in DCM (1 mL) was added 1M DCM solution of 2-chloroacetyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-14. (29 mg, 76%). LC-MS (ESI) m/z: 349 $[M+1]^+$. 1H NMR (500 MHz, DMSO-d6) δ 8.57 (t, J=6.0 Hz, 1H), 7.44 (s, 1H), 7.25 (s, 1H), 7.13 (d, J=7.8 Hz, 1H), 7.04 (dd, J=8.2, 1.5 Hz, 1H), 6.95 (ddd, J=8.5, 7.3, 1.6 Hz, 1H), 4.94 (s, 1H), 4.68 (s, 1H), 4.56 (d, J=13.6 Hz, 1H), 4.11 (d, J=5.8 Hz, 2H), 4.08-3.85 (m, 2H), 3.76 (s, 3H).

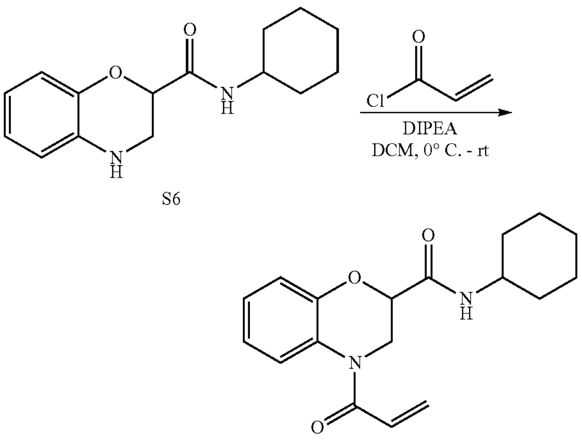

S6

JWZ-1-12

JWZ-1-12: To ice cooled mixture of S6 (30 mg, 0.11 mmol) and DIPEA (1.5 eq) in DCM (1 mL) was added 1M DCM solution of acryloyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-14. (22 mg, 65%). LC-MS (ESI) m/z: 315 $[M+1]^+$. 1H NMR (500 MHz, DMSO-d6) δ 7.90 (d, J=8.1 Hz, 1H), 7.13 (td, J=7.8, 7.2, 1.6 Hz, 1H), 7.04 (dd, J=8.2, 1.5 Hz, 1H), 6.97-6.88 (m, 1H), 6.65 (d, J=14.3 Hz, 1H), 6.24 (dd, J=16.9, 2.0 Hz, 1H), 5.81 (dd, J=10.4, 2.1 Hz, 1H), 4.84 (dd, J=5.1, 3.5 Hz, 1H), 4.18 (dd, J=13.5, 5.1 Hz, 1H), 3.89 (dd, J=13.5, 3.5 Hz, 1H), 3.54-3.48 (m, 1H), 1.72-1.50 (m, 4H), 1.30-1.00 (m, 5H).

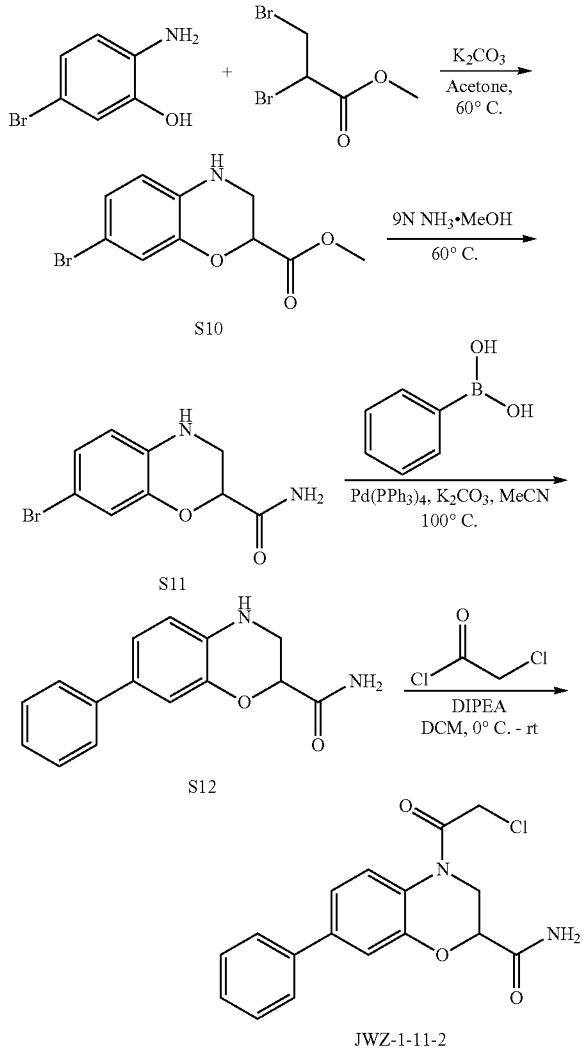

S10

S11

S12

JWZ-1-11-2

S10: To a mixture of 2-amino-5-bromophenol (1 mmol, 1.0 eq), and K2CO3 (3 mmol, 3.0 eq) in acetone (5 mL) was added methyl 2,3-dibromopropanoate (1.1 mmol, 1.1 eq) at room temperature. The mixture was stirred at 60 C for 8 hours. The solution was concentrated and purified via silica gel flash chromatography to afford s10 (206 mg, 76%) as yellow solid LC-MS (ESI) m/z: 272 $[M+1]^+$.

S11: S10 (0.76 mmol, 1.0 eq) was dissolved in 4 mL 9N NH3 MeOH solvent. The mixture was stirred at 60 C for 8 hours. The solution was concentrated and purified via silica gel flash chromatography to afford s11 (162 mg, 83%) as yellow solid LC-MS (ESI) m/z: 257 $[M+1]^+$.

S12: The mixture of S11 (60 mg, 0.22 mmol, 1.0 eq), Pd(PPh3)4 (0.05 eq) and K2CO3 (3.0 eq) in MeCN (1 mL) under N2 protection was stirred at 100 C for 8 hours. The solution was filtered and concentrated and purified via silica gel flash chromatography to afford s12 (45 mg, 81%) as yellow solid LC-MS (ESI) m/z: 255 $[M+1]^+$.

JWZ-1-11-2: To ice cooled mixture of S12 (15 mg, 0.06 mmol) and DIPEA (1.5 eq) in DCM (1 mL) was added 1M DCM solution of acryloyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-14. (15 mg, 79%).

LC-MS (ESI) m/z: 331 $[M+1]^+$. 1H NMR (500 MHz, DMSO-d6) δ 7.73-7.58 (m, 4H), 7.48 (t, J=7.7 Hz, 2H), 7.41-7.35 (m, 1H), 7.33 (d, J=2.1 Hz, 1H), 7.27 (dd, J=8.5, 2.2 Hz, 1H), 4.86 (d, J=92.0 Hz, 3H), 4.63 (d, J=13.9 Hz, 2H).

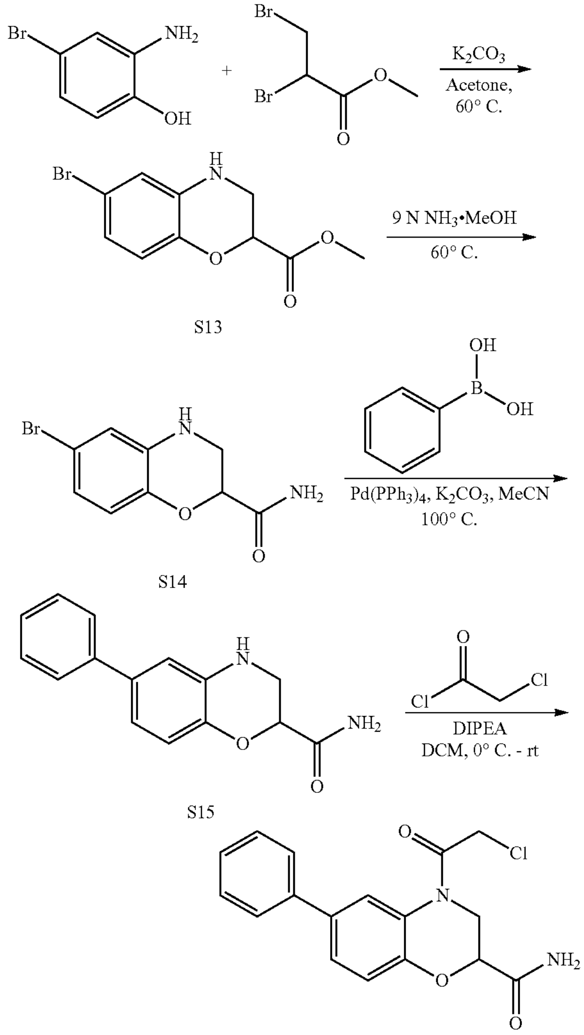

S13

S14

S15

JWZ-1-15

S13: To a mixture of 2-amino-4-bromophenol (1 mmol, 1.0 eq), and K2CO3 (3 mmol, 3.0 eq) in acetone (5 mL) was added methyl 2,3-dibromopropanoate (1.1 mmol, 1.1 eq) at room temperature. The mixture was stirred at 60 C for 8 hours. The solution was concentrated and purified via silica gel flash chromatography to afford s10 (210 mg, 78%) as yellow solid LC-MS (ESI) m/z: 272 $[M+1]^+$.

S14: S13 (0.78 mmol, 1.0 eq) was dissolved in 4 mL 9N NH3 MeOH solvent. The mixture was stirred at 60 C for 8 hours. The solution was concentrated and purified via silica gel flash chromatography to afford s11 (159 mg, 80%) as yellow solid LC-MS (ESI) m/z: 257 $[M+1]^+$.

S15: The mixture of S14 (60 mg, 0.22 mmol, 1.0 eq), Pd(PPh3)$_4$ (0.05 eq) and K2CO3 (3.0 eq) in MeCN (1 mL) under N2 protection was stirred at 100 C for 8 hours. The solution was filtered and concentrated and purified via silica gel flash chromatography to afford s12 (49 mg, 83%) as yellow solid LC-MS (ESI) m/z: 255 $[M+1]^+$.

JWZ-1-11-2: To ice cooled mixture of S15 (15 mg, 0.06 mmol) and DIPEA (1.5 eq) in DCM (1 mL) was added 1M DCM solution of acryloyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-14. (14 mg, 78%). LC-MS (ESI) m/z: 331 $[M+1]^+$. 1H NMR (500 MHz, DMSO-d6) δ 7.70 (s, 1H), 7.69-7.53 (m, 4H), 7.50-7.42 (m, 3H), 7.39-7.30 (m, 1H), 7.24-6.96 (m, 1H), 4.86 (d, J=79.8 Hz, 2H), 4.67 (d, J=13.8 Hz, 1H), 4.11 (s, 2H).

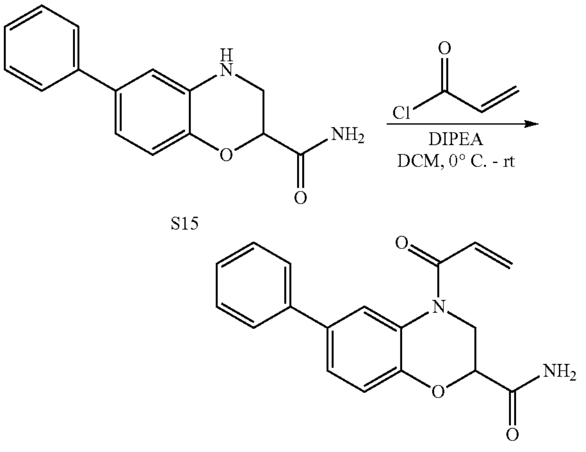

S15

JWZ-1-25

JWZ-1-25: To ice cooled mixture of S15 (15 mg, 0.06 mmol) and DIPEA (1.5 eq) in DCM (1 mL) was added 1M DCM solution of acryloyl chloride (1.1 eq) dropwise, the mixture was stirred and allowed to warm to room temperature over 0.5 hour. LC-MS indicated formation of desired product. The mixture was concentrated and purified via prep-HPLC to afford compound JWZ-1-25. (15 mg, 85%). LC-MS (ESI) m/z: 309 $[M+1]^+$. 1H NMR (500 MHz, DMSO-d6) δ 7.65-7.59 (m, 2H), 7.60-7.54 (m, 3H), 7.49 (s, 1H), 7.45 (dd, J=8.7, 6.9 Hz, 2H), 7.37-7.29 (m, 1H), 7.13 (d, J=8.5 Hz, 1H), 6.79 (dd, J=16.7, 10.4 Hz, 1H), 6.27 (dd, J=16.8, 2.1 Hz, 1H), 5.86 (dd, J=10.4, 2.1 Hz, 1H), 4.90 (dd, J=5.1, 3.4 Hz, 2H), 4.10 (ddd, J=133.6, 13.5, 4.3 Hz, 2H).

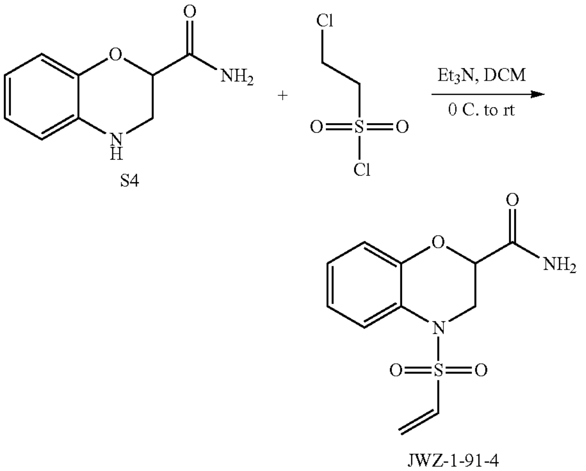

S4

JWZ-1-91-4

JWZ-1-94-1: To ice cooled mixture of S4 (80 mg) and Et3N (1.5 eq) in DCM (1 mL) was added 1M DCM solution of 2-chloroethane-1-sulfonyl chloride (1.1 eq) dropwise, the mixture was stirred and allowed to warm to room temperature over 3 hour. LC-MS indicated formation of desired product. The mixture was concentrated and purified via prep-HPLC to afford compound JWZ-1-94-1. (19 mg). LC-MS (ESI) m/z: 269 $[M+1]^+$. 1H NMR (500 MHz, DMSO-d6) δ 7.66 (d, J=40.1 Hz, 2H), 7.52 (dd, J=8.3, 1.5 Hz, 1H), 7.15-7.02 (m, 2H), 6.97-6.86 (m, 2H), 6.26-6.14 (m, 2H), 4.67 (dd, J=8.4, 3.1 Hz, 1H), 4.16 (dd, J=14.1, 3.1 Hz, 1H), 3.65 (dd, J=14.1, 8.4 Hz, 1H).

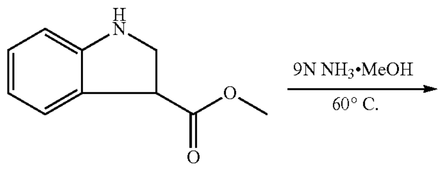

S17

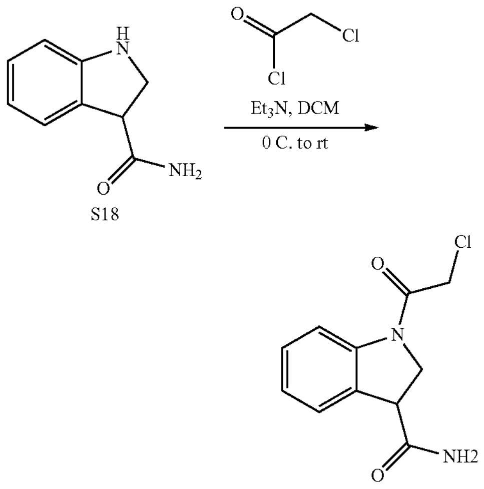

S18

JWZ-1-95-2

S17 (0.5 mmol, 1.0 eq) was dissolved in 4 mL 9N NH3 MeOH solvent. The mixture was stirred at 60 C for 8 hours. The solution was concentrated and purified via silica gel flash chromatography to afford s18 (60 mg, 74%) as yellow solid LC-MS (ESI) m/z: 163 $[M+1]^+$.

JWZ-1-95-2: To ice cooled mixture of S8 (25 mg) and Et3N (1.5 eq) in DCM (1 mL) was added 1M DCM solution of 2-chloroethane-1-sulfonyl chloride (1.1 eq) dropwise, the mixture was stirred and allowed to warm to room temperature over 3 hour. LC-MS indicated formation of desired product. The mixture was concentrated and purified via prep-HPLC to afford compound JWZ-1-95-2. (19 mg). LC-MS (ESI) m/z: 239 $[M+1]^+$. $^1$H NMR (500 MHz, $DMSO-d_6$) δ 8.06 (d, J=8.1 Hz, 1H), 7.85 (s, 1H), 7.38 (d, J=7.5 Hz, 1H), 7.30-7.21 (m, 2H), 7.09 (td, J=7.5, 1.1 Hz, 1H), 4.62-4.49 (m, 2H), 4.38 (dd, J=9.8, 5.5 Hz, 1H), 4.31-4.14 (m, 2H), 2.08 (s, 1H).

Synthesis of B-1

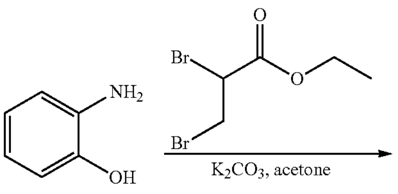

1

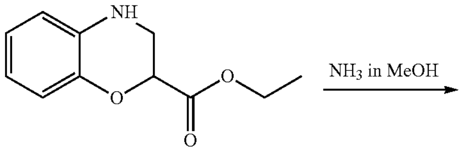

3

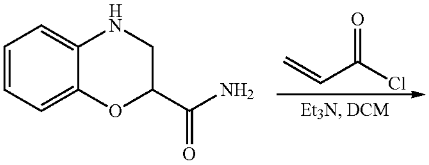

4

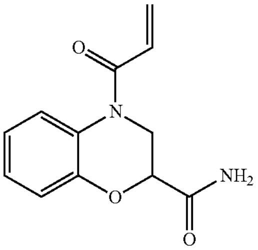

B-1

Step 1: Synthesis of ethyl 3,4-dihydro-2H-benzo[b][1,4]oxazine-2-carboxylate (Compound 3)

To 2-aminophenol (1) (8 g, 31 mmol) in acetone (35 mL) was added $K_2CO_3$ (5.1 g, 37 mmol) and ethyl 2,3-dibromopropanoate (3.4 g, 31 mmol). The mixture was stirred at 60° C. under N2 for 16 hours, after cooled down to rt the mixture was diluted with water (20 mL) and extracted with EtOAc (3×50 mL). The combined organic phases were washed with saturated $NaHCO_3$ solution (40 mL) and brine (40 mL), dried over anhydrous $Na_2SO_4$, concentrated and purified with flash column chromatography on silica gel (ethyl acetate in petroleum ether, from 0% to 30%, v/v) to furnish Compound (3) as a yellow oil (2.4 g, yield 37%). LC-MS (ESI) m/z: 208 $[M+H]^+$.

Step 2: Synthesis of 3,4-dihydro-2H-benzo[b][1,4]oxazine-2-carboxamide (Compound 4)

A mixture of compound (3) (780 mg, 3.66 mmol) and $NH_3$ solution (7 M solution in methanol, 1 mL) was heated in a sealed tube at 70° C. for 15 hours. The mixture was concentrated to leave the crude Compound (4) as a light yellow oil (170 mg, crude), which was used directly in the next step. LC-MS (ESI) m/z: 179 $[M+H]^+$;

Step 3: Synthesis of 4-acryloyl-3,4-dihydro-2H-benzo[b][1,4]oxazine-2-carboxamide (Compound B-1)

The mixture of compound (4) (178 mg, 1 mmol) and $Et_3N$ (202 mg, 1 mmol) in dichloromethane (10 mL) under $N_2$ was cooled to 0° C., and then acryloyl chloride (90 mg, 1 mmol) was added. The mixture was stirred at 0° C. for 2 hours, concentrated and purified with reverse phase column chromatography to furnish Compound B-1 as a white solid (120 mg, yield 52% for two steps). LC-MS (ESI) m/z: 233 $[M+H]^+$; $^1H$-NMR (DMSO-$d_6$, 400 MHz): δ (ppm) 3.81-3.86 (m, 1H), 4.21 (dd, $J_1$=4.8 Hz, $J_2$=13.6 Hz, 1H), 4.83 (dd, $J_1$=3.6 Hz, $J_2$=5.2 Hz, 1H), 5.80 (dd, $J_1$=1.6 Hz, $J_2$=9.6 Hz, 1H), 6.22 (dd, $J_1$=1.6 Hz, $J_2$=16.8 Hz, 1H), 6.61-6.68 (m, 1H), 6.91 (t, J=8.4 Hz, 1H), 7.03 (d, J=8 Hz, 1H), 7.11 (t, J=7.6 Hz, 1H), 7.20-7.46 (brs, 1H).

Synthesis of B-2

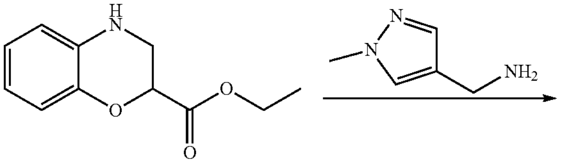

from B-1

1

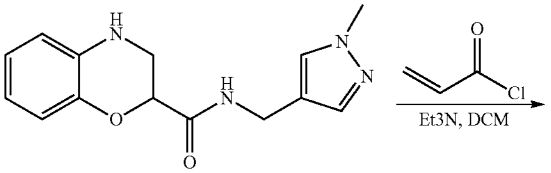

2

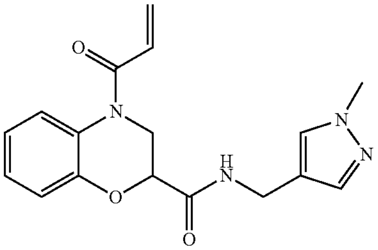

B-2

Step 1: Synthesis of N-((1-methyl-1H-pyrazol-4-yl)methyl)-3,4-dihydro-2H-benzo[b][1,4]oxazine-2-carboxamide (Compound 2)

The mixture of compound (1) (514 mg, 2 mmol) and (1-methyl-1H-pyrazol-4-yl) methanamine (444 mg, 4 mmol) in EtOH (2 mL) was heated in a sealed tube at 110° C. for 2 days. The mixture was concentrated and purified with flash column chromatography on silica gel (ethyl acetate in petroleum ether, from 0% to 100%, v/v) to leave the crude Compound (2) as a light yellow oil (1 g, crude), which was used directly in the next step. LC-MS (ESI) m/z: 273$[M+H]^+$;

Step 2: Synthesis of 4-acryloyl-N-((1-methyl-1H-pyrazol-4-yl)methyl)-3,4-dihydro-2H-benzo[b][1,4]oxazine-2-carboxamide (Compound B-2)

The mixture of compound (2) (530 mg, 1 mmol) and $Et_3N$ (404 mg, 4 mmol) in dichloromethane (10 mL) under $N_2$ was cooled down to 0° C., and then acryloyl chloride (175 mg, 2 mmol) was added. The mixture was stirred at 20° C. for 2 hours, concentrated and purified with reverse phase column chromatography to furnish Compound (B-2) as colorless oil (120 mg, yield 37% for two steps). LC-MS (ESI) m/z: 327.1

$[M+H]^+$; $^1$H-NMR (DMSO-$d_6$, 400 MHz): δ (ppm) 3.74 (s, 3H), 3.94 (dd, $J_1$=3.2 Hz, $J_2$=14 Hz, 1H), 4.02-4.11 (m, 3H), 4.87-4.89 (m, 1H), 5.80 (dd, $J_1$=2 Hz, $J_2$=10.4 Hz, 1H), 6.24 (dd, $J_1$=2.4 Hz, $J_2$=16.8 Hz, 1H), 6.59-6.71 (brs, 1H), 6.92 (t, J=8.4 Hz, 1H), 7.03 (d, J=8 Hz, 1H), 7.12 (t, J=8.4 Hz, 1H), 7.35-7.44 (brs, 3H), 8.49 (t, J=5.6 Hz, 1H).

Synthesis of B-4

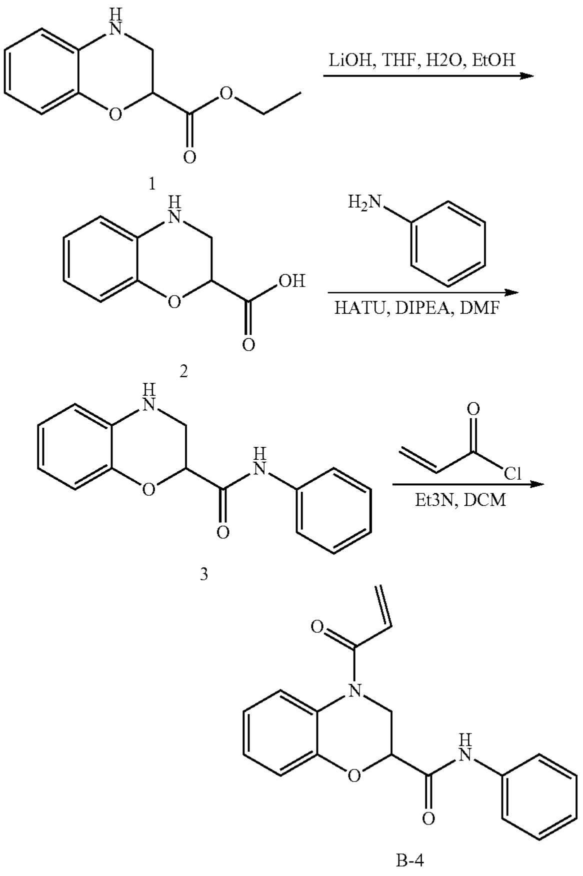

Step 1: Synthesis of 3,4-dihydro-2H-benzo[b][1,4]oxazine-2-carboxylic acid (Compound 2)

To the mixture of compound (1) (416 mg, 2 mmol) in THF (2 mL), EtOH (2 mL) and $H_2O$ (2 mL) was added LiOH·$H_2O$ (168 mg, 4 mmol). The mixture was stirred at 20° C. for 2 hours, and then concentrated under vacuum to leave the crude Compound (2) as a yellow solid (360 mg, crude). LC-MS (ESI) m/z: 180 $[M+H]^+$.

Step 2: Synthesis of N-phenyl-3,4-dihydro-2H-benzo[b][1,4]oxazine-2-carboxamide (Compound 3)

A mixture of compound (2) (360 mg, 2 mmol), aniline (186 mg, 2 mmol), HATU (760 mg, 2 mmol) and DIPEA (387 mg, 3 mmol) in DMF (4 mL) was stirred at 20° C. for 15 hours. The mixture was diluted with water (20 mL) and extracted with EtOAc (2×20 mL). The combined organic phases were washed with saturated $NaHCO_3$ solution (40 mL) and brine (40 mL), dried over anhydrous $Na_2SO_4$, concentrated and purified with flash column chromatography on silica gel (ethyl acetate in petroleum ether, from 0% to 30%, v/v) to furnish Compound (3) as a light yellow oil (380 mg, 75% for two steps). LC-MS (ESI) m/z: 255 $[M+H]^+$;

Step 3: Synthesis of 4-acryloyl-N-phenyl-3,4-dihydro-2H-benzo[b][1,4]oxazine-2-carboxamide (Compound B-4)

The solution of compound (3) (380 mg, 1.5 mmol) and $Et_3N$ (303 mg, 3 mmol) in dichloromethane (10 mL) under N2 was cooled down to 0° C., and then acryloyl chloride (136 mg, 1.5 mmol) was added. The mixture was stirred at 0° C. for 2 hours, concentrated and purified with reverse phase column chromatography to furnish Compound (B-4) as a white solid (274 mg, yield 59%). LC-MS (ESI) m/z: 309.1 $[M+H]^+$; $^1$H-NMR (DMSO-$d_6$, 400 MHz): δ (ppm) 3.99 (dd, $J_1$=4 Hz, $J_2$=13.6 Hz, 1H), 4.35 (dd, $J_1$=4.8 Hz, $J_2$=13.6 Hz, 1H), 5.08 (t, J=4 Hz, 1H), 5.79 (dd, $J_1$=2 Hz, $J_2$=10.4 Hz, 1H), 6.21 (dd, $J_1$=2 Hz, $J_2$=16.8 Hz, 1H), 6.64-6.74 (m, 1H), 6.94 (t, J=8 Hz, 1H), 7.05-7.15 (m, 3H), 7.30 (t, J=8 Hz, 2H), 7.53 (t, J=7.6 Hz, 2H), 10.13 (s, 1H).

Synthesis of B-6.

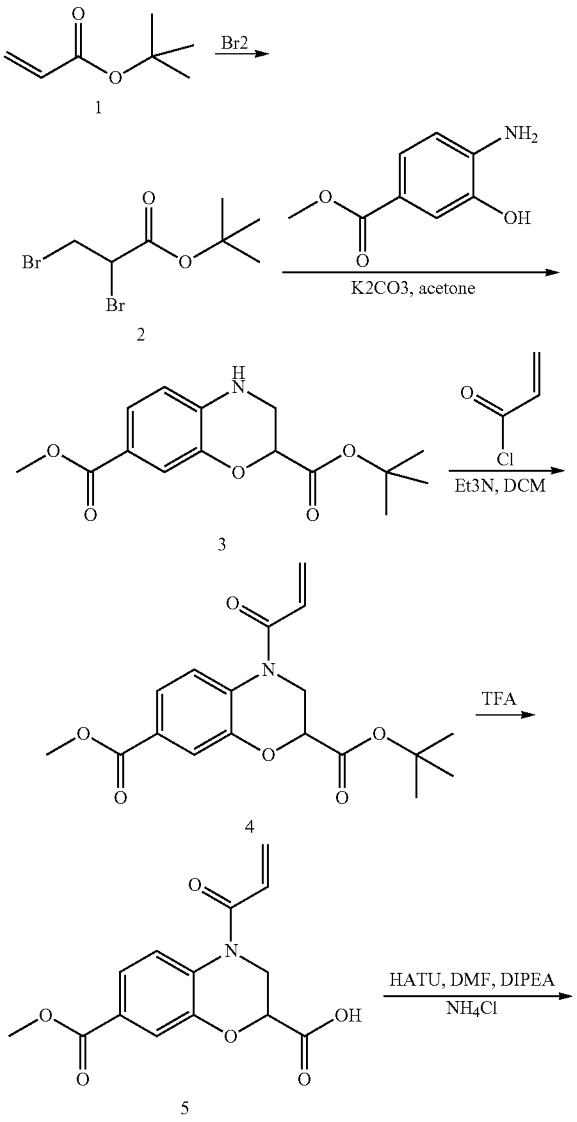

-continued

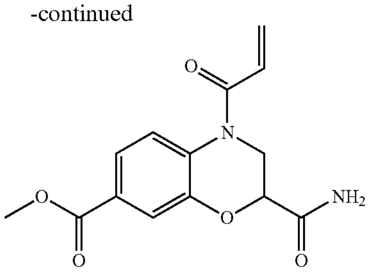

B-6

Step 1: Synthesis of tert-butyl 2,3-dibromopropanoate (Compound 2)

The solution of tert-butyl acrylate (1) (11.4 mL, 7.8 mmol) in dichloromethane (100 mL) was cooled down to 0° C., and then $Br_2$ (4 mL, 7.8 mmol) was added dropwise. The mixture was warmed gradually to 25° C. and stirred at 25° C. for 16 hours. The mixture was washed with brine (40 mL), dried over anhydrous $Na_2SO_4$, filtered and concentrated to leave the crude Compound (2) as a light yellow oil. (18 g, yield 80%).

Step 2: Synthesis of 2-(tert-butyl) 7-methyl 3,4-dihydro-2H-benzo[b][1,4]oxazine-2,7-dicarboxylate (Compound 3)

To the solution of methyl 4-amino-3-hydroxybenzoate (3.34 g, 20 mmol) in acetone (30 mL) was added $K_2CO_3$ (3.3 g, 24 mmol) and Compound (2) (5.8 g, 20 mmol). The mixture was stirred at 60° C. under $N_2$ for 40 hours. After cooled down to rt the mixture was diluted with water (50 mL) and extracted with EtOAc (3×50 mL). The combined organic phases were washed with saturated $NaHCO_3$ solution (40 mL) and brine (40 mL), dried over anhydrous $Na_2SO_4$, concentrated and purified with flash column chromatography on silica gel (ethyl acetate in petroleum ether, from 0% to 20%, v/v) to furnish Compound (3) as a yellow solid (1.3 g, yield 22%). LC-MS (ESI) m/z: 294 $[M+H]^+$.

Step 3: Synthesis of 2-(tert-butyl) 7-methyl 4-acryloyl-3,4-dihydro-2H-benzo[b][1,4]oxazine-2,7-dicarboxylate (Compound 4)

The solution of compound (3) (294 mg, 1 mmol) and $Et_3N$ (202 mg, 1 mmol) in dichloromethane (10 mL) was cooled down to 0° C., and then acryloyl chloride (90 mg, 1 mmol) was added. The mixture was stirred at 0° C. for 2 hours, concentrated and purified with flash column chromatography on silica gel (ethyl acetate in petroleum ether, from 0% to 20%, v/v) to furnish Compound (4) as a yellow oil (300 mg, 86%). LC-MS (ESI) m/z: 348 $[M+H]^+$; $^1$H-NMR (DMSO-$d_6$, 400 MHz): δ (ppm) 1.31 (s, 9H), 3.58 (d, J=12 Hz, 1H), 3.84 (s, 3H), 4.74 (d, J=14 Hz, 1H), 5.23-5.24 (m, 1H), 5.90 (dd, $J_1$=2 Hz, $J_2$=10.4 Hz, 1H), 6.32 (dd, $J_1$=2 Hz, $J_2$=16.8 Hz, 1H), 6.68-6.75 (m, 1H), 7.05-7.51 (m, 3H).

Step 4: Synthesis of 4-acryloyl-7-(methoxycarbonyl)-3,4-dihydro-2H-benzo[b]-[1,4]oxazine-2-carboxylic acid (Compound 5)

The mixture of compound (4) (300 mg, 0.86 mmol) and TFA (2 mL) was stirred at 20° C. for 2 hours, and then concentrated under vacuum, the residue was purified with preparative HPLC to give Compound (5) as yellow oil (170 mg, 68%). LC-MS (ESI) m/z: 292 $[M+H]^+$; Step 5: Synthesis of methyl 4-acryloyl-2-carbamoyl-3,4-dihydro-2H-benzo[b]=[1,4]oxazine-7-carboxylate (Compound B-6)

The mixture of compound (5) (170 mg, 0.58 mmol), $NH_4Cl$ (62 mg, 1.16 mmol), HATU (331 mg, 0.87 mmol) and DIPEA (224 mg, 1.74 mmol) in DMF (2 mL) was stirred in a sealed tube at 20° C. for 15 hours. The mixture was purified directly with preparative HPLC to furnish Compound B-6 as a white solid (23 mg, yield 14%). LC-MS (ESI) m/z: 291 $[M+H]^+$; $^1$H-NMR (DMSO-$d_6$, 400 MHz): δ (ppm) 3.84 (s, 3H), 3.95 (dd, $J_1$=3.2 Hz, $J_2$=13.6 Hz, 1H), 4.20 (dd, $J_1$=5.2 Hz, $J_2$=13.6 Hz, 1H), 4.92 (dd, $J_1$=3.6 Hz, $J_2$=4.8 Hz, 1H), 5.86 (dd, $J_1$=1.6 Hz, $J_2$=10.4 Hz, 1H), 6.27 (dd, $J_1$=2 Hz, $J_2$=16.8 Hz, 1H), 6.68-6.75 (m, 1H), 7.49-7.60 (m, 4H), 7.69 (s, 1H).

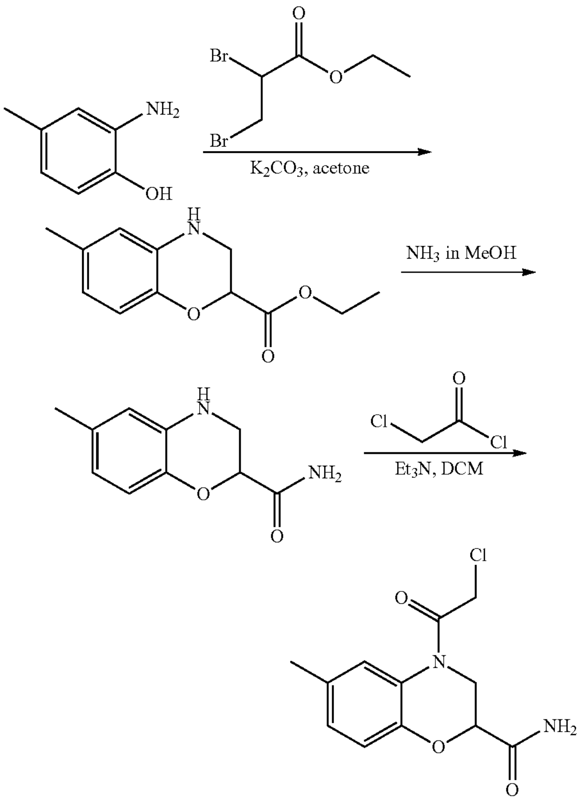

ND-30

Synthesis of 4-(2-chloroacetyl)-6-methyl-3,4-dihydro-2H-benzo[b][1,4]oxazine-2-carboxamide (ND-30)

2,3-Dibromopropionic methyl ester (100 mg), potassium carbonate (460 mg) and 6-Amino-m-Cresol (137 mg) was dissolved in acetone (4 mL) and refluxed overnight. The resulting solid was filtered out, and the reaction was diluted with dichloromethane and wash with 1 M HCl, $NaHCO_3$, brine, dried over sodium sulfate and concentrated down. The resulting product was then dissolved in THF (2 mL) and 2M ammonium in ethanol (5 mL) and refluxed overnight. The solution was then reduced and purified via prep-HPLC to yield 42 mg of product. To 16 mg product above was added acetonitrile (1.5 mL), triethylamine (25 uL) and chloroacetyl chloride (20 uL) and allowed to stir for 2 hours. At that time the solution was acidified with 20% formic acid and the solution was then reduced and purified via prep-HPLC to yield 8.7 mg of product. Theoretical mass 269.06875, Observed mass 269.06836.

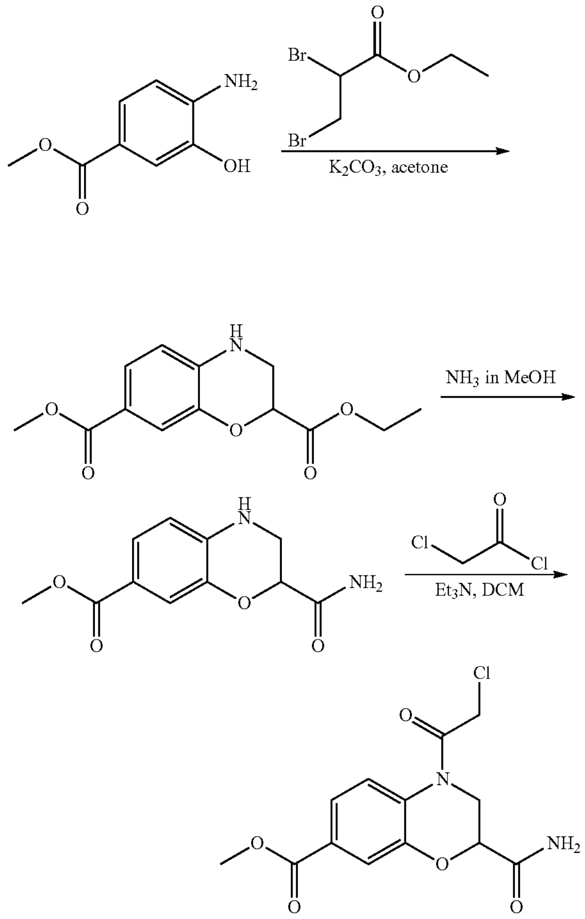

ND-31

Synthesis of methyl 2-carbamoyl-4-(2-chloro-acetyl)-3,4-dihydro-2H-benzo[b][1,4]oxazine-7-carboxylate (ND-31)

2,3-Dibromopropionic methyl ester (100 mg), potassium carbonate (460 mg), and methyl 3-amino 4-hydroxybenzoatel (186 mg) was dissolved in acetone (4 mL) and refluxed overnight. The resulting solid was filtered out, and the reaction was diluted with dichloromethane and wash with 1 M HCl, $NaHCO_3$, brine, dried over sodium sulfate and concentrated down. The resulting product was then dissolved in THF (2 mL) and 2M ammonium in ethanol (5 mL) and refluxed overnight. The solution was then reduced and purified via prep-HPLC to yield 65 mg of product. To 16 mg product above was added acetonitrile (1.5 mL), triethylamine (25 uL) and chloroacetyl chloride (20 uL) and allowed to stir for 2 hours. At that time the solution was acidified with 20% formic acid and the solution was then reduced and purified via prep-HPLC to yield 6.9 mg of product. Theoretical mass 313.05858, Observed mass 313.05817.

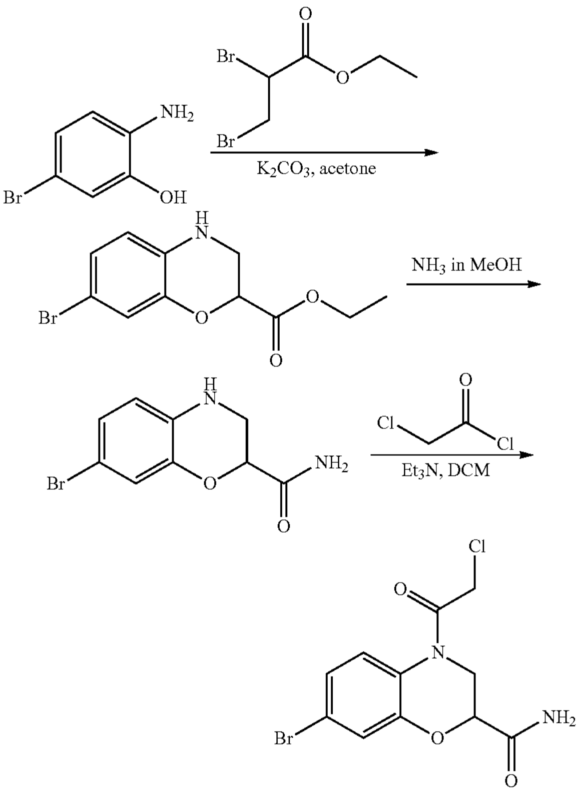

ND-32

Synthesis of 7-bromo-4-(2-chloroacetyl)-3,4-dihydro-2H-benzo[b][1,4]oxazine-2-carboxamide (ND-32)

2,3-Dibromopropionic methyl ester (100 mg), potassium carbonate (460 mg), and 2-amino-5-bromophenol (155 mg) was dissolved in acetone (4 mL) and refluxed overnight. The resulting solid was filtered out, and the reaction was diluted with dichloromethane and wash with 1 M HCl, $NaHCO_3$, brine, dried over sodium sulfate and concentrated down. The resulting product was then dissolved in THF (2 mL) and 2M ammonium in ethanol (5 mL) and refluxed overnight. The solution was then reduced and purified via prep-HPLC to yield 67 mg of product. To 16 mg product above was added acetonitrile (1.5 mL), triethylamine (25 uL) and chloroacetyl chloride (20 uL) and allowed to stir for 2 hours. At that time the solution was acidified with 20% formic acid and the solution was then reduced and purified via prep-HPLC to yield 11.9 mg of product. Theoretical mass 332.96361, Observed mass 332.96345.

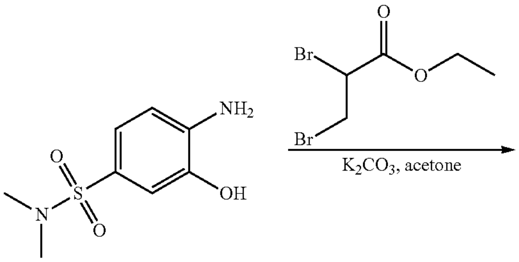

-continued

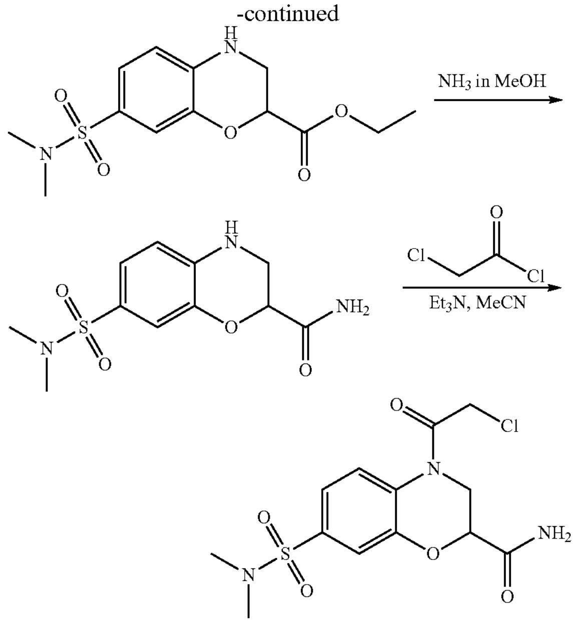

ND-33

Synthesis of 4-(2-chloroacetyl)-7-(N,N-dimethylsulfamoyl)-3,4-dihydro-2H-benzo[b][1,4]oxazine-2-carboxamide (ND-33)

2,3-Dibromopropionic methyl ester (100 mg), potassium carbonate (460 mg), and 4-amino-3-hydroxy-N,N-dimethylbenzenesulfonamide (241 mg) was dissolved in acetone (4 mL) and refluxed overnight. The resulting solid was filtered out, and the reaction was diluted with dichloromethane and wash with 1 M HCl, $NaHCO_3$, brine, dried over sodium sulfate and concentrated down. The resulting product was then dissolved in THF (2 mL) and 2M ammonium in ethanol (5 mL) and refluxed overnight. The solution was then reduced and purified via prep-HPLC to yield 65 mg of product. To 16 mg product above was added acetonitrile (1.5 mL), triethylamine (25 uL) and chloroacetyl chloride (20 uL) and allowed to stir for 2 hours. At that time the solution was acidified with 20% formic acid and the solution was then reduced and purified via prep-HPLC to yield 3.4 mg of product. Theoretical mass 362.05720, Observed mass 362.05677.

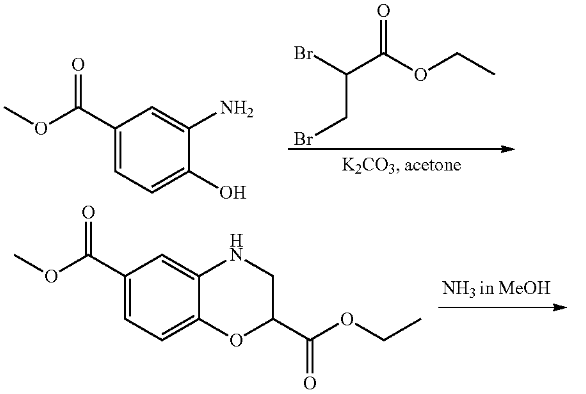

-continued

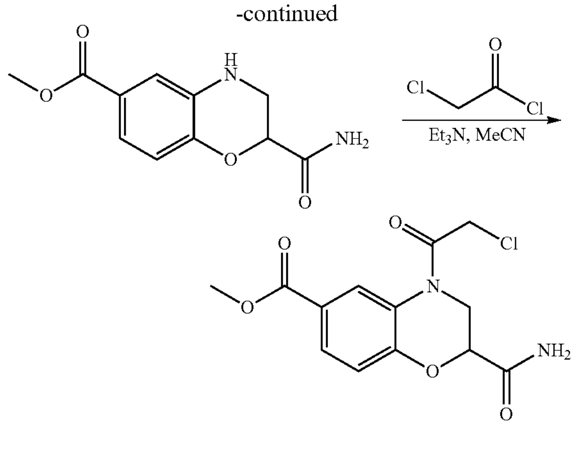

ND-34

Synthesis of methyl 2-carbamoyl-4-(2-chloroacetyl)-3,4-dihydro-2H-benzo[b][1,4]oxazine-6-carboxylate (ND-34)

2,3-Dibromopropionic methyl ester (100 mg), potassium carbonate (460 mg), and 4-amino-3-hydroxy-N,N-dimethylbenzenesulfonamide (186 mg) was dissolved in acetone (4 mL) and refluxed overnight. The resulting solid was filtered out, and the reaction was diluted with dichloromethane and wash with 1 M HCl, $NaHCO_3$, brine, dried over sodium sulfate and concentrated down. The resulting product was then dissolved in THF (2 mL) and 2M ammonium in ethanol (5 mL) and refluxed overnight. The solution was then reduced and purified via prep-HPLC to yield 50 mg of product. To 16 mg product above was added acetonitrile (1.5 mL), triethylamine (25 uL) and chloroacetyl chloride (20 uL) and allowed to stir for 2 hours. At that time the solution was acidified with 20% formic acid and the solution was then reduced and purified via prep-HPLC to yield 3 mg of product. Theoretical mass 313.05858, Observed mass 313.05823.

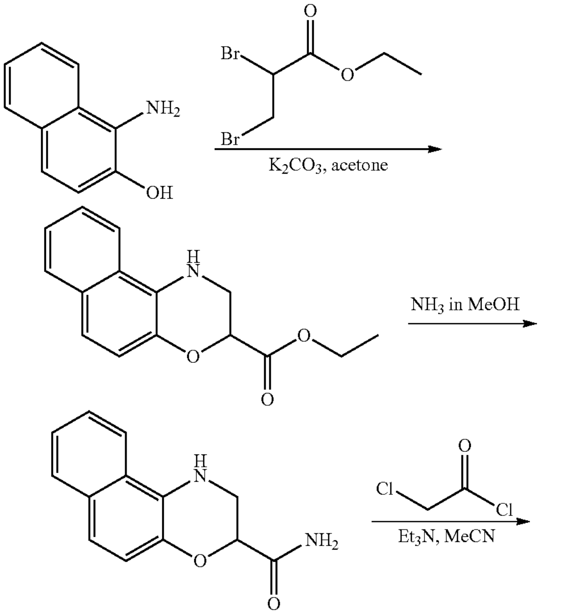

-continued

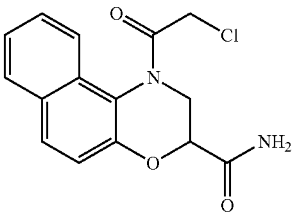

ND-35

Synthesis of 1-(2-chloroacetyl)-2,3-dihydro-1H-naphtho[2,1-b][1,4]oxazine-3-carboxamide (ND-35)

2,3-Dibromopropionic methyl ester (100 mg), potassium carbonate (460 mg), 1-Amino-2-naphthol hydrochloride (218 mg) were dissolved in acetone (4 mL) and refluxed overnight. Afterwards the solid was filtered, and the reaction was diluted with dichloromethane and wash with 1 M HCl, $NaHCO_3$, brine, dried over sodium sulfate and concentrated down. The resulting product was then dissolved in THF (2 mL) and 7M ammonium in methanol (5 mL) and refluxed overnight. The solution was then reduced and purified using reverse phase HPLC. Buffer A was water with 0.035% trifluoroacetic acid and Buffer B was methanol with 0.035% trifluoroacetic acid. The method was 5% buffer B for 5 mins which was then a ramp to 99% Buffer B over 55 mins. Yield was 66 mg. 16 mg of the above compound was then dissolved in acetonitrile (1.5 mL), triethylamine (25 uL) and then chloroacetyl chloride (20 uL) was added and allowed to stir for 2 hours. At that time the solution was acidified with 20% formic acid, filtered and purified by reverse phase HPLC. Buffer A was water with 0.035% trifluoroacetic acid and Buffer B was methanol with 0.035% trifluoroacetic acid. The method was 15% buffer B for 5 mins which was then a ramp to 99% Buffer B over 45 mins. Yield is 3.0 mg. Theoretical mass 305.06875, Observed mass 305.06854.

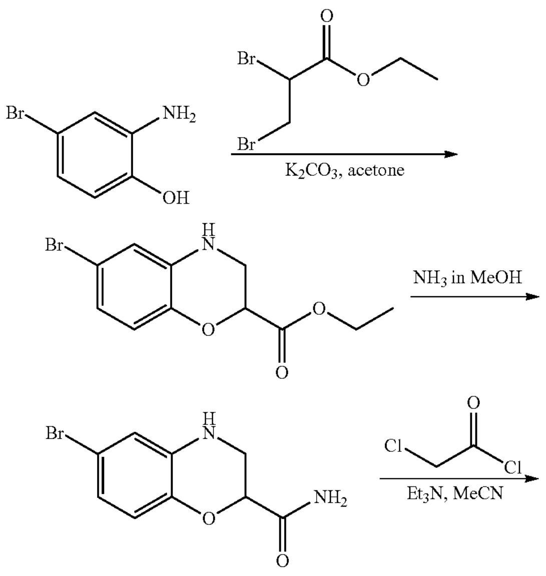

-continued

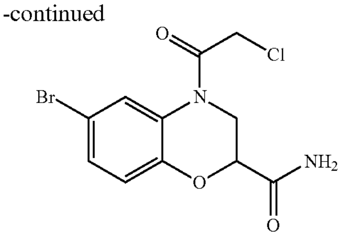

ND-36

Synthesis of 6-bromo-4-(2-chloroacetyl)-3,4-dihydro-2H-benzo[b][1,4]oxazine-2-carboxamide (ND-36)

2,3-Dibromopropionic methyl ester (100 mg), potassium carbonate (460 mg), and 2-amino-4-bromophenol (209 mg) was dissolved in acetone (4 mL) and refluxed overnight. The resulting solid was filtered out, and the reaction was diluted with dichloromethane and wash with 1 M HCl, $NaHCO_3$, brine, dried over sodium sulfate and concentrated down. The resulting product was then dissolved in THF (2 mL) and 2M ammonium in ethanol (5 mL) and refluxed overnight. The solution was then reduced and purified via prep-HPLC to yield 67 mg of product. To 16 mg product above was added acetonitrile (1.5 mL), triethylamine (25 uL) and chloroacetyl chloride (20 uL) and allowed to stir for 2 hours. At that time the solution was acidified with 20% formic acid and the solution was then reduced and purified via prep-HPLC to yield 11.5 mg of product. Theoretical mass 332.96361, Observed mass 332.96353.

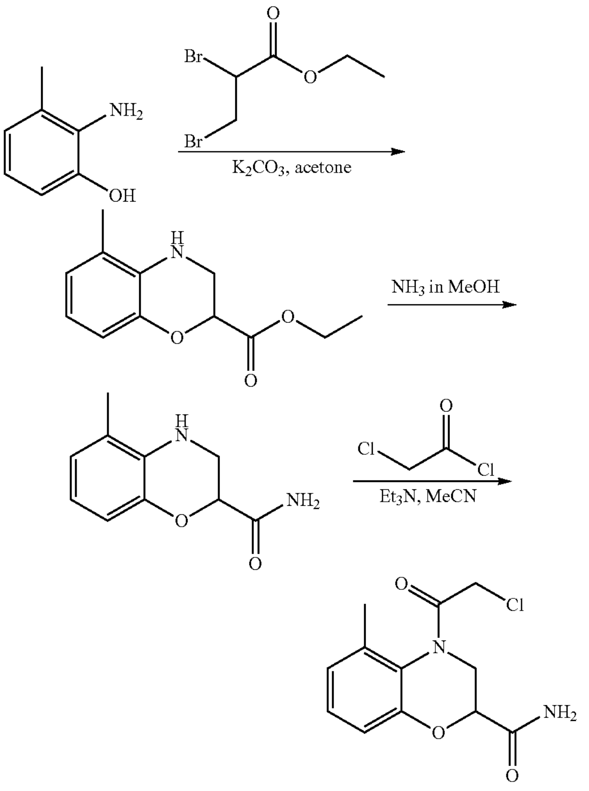

ND-37

Synthesis of 4-(2-chloroacetyl)-5-methyl-3,4-dihydro-2H-benzo[b][1,4]oxazine-2-carboxamide (ND-37)

2,3-Dibromopropionic methyl ester (100 mg), potassium carbonate (460 mg), and 2-amino-3-methylphenol (137 mg) was dissolved in acetone (4 mL) and refluxed overnight. The resulting solid was filtered out, and the reaction was diluted with dichloromethane and wash with 1 M HCl, $NaHCO_3$, brine, dried over sodium sulfate and concentrated down. The resulting product was then dissolved in THF (2 mL) and 2M ammonium in ethanol (5 mL) and refluxed overnight. The solution was then reduced and purified via prep-HPLC to yield 25 mg of product. To 16 mg product above was added acetonitrile (1.5 mL), triethylamine (25 uL) and chloroacetyl chloride (20 uL) and allowed to stir for 2 hours. At that time the solution was acidified with 20% formic acid and the solution was then reduced and purified via prep-HPLC to yield 1 mg of product. Theoretical mass 269.06875, Observed mass 269.06844.

Synthesis of Compound 6

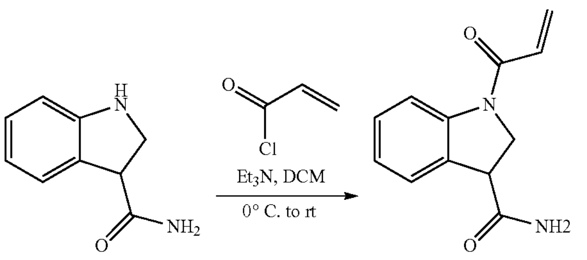

S18 6

To ice cooled mixture of S18 (15 mg) and Et3N (1.5 eq) in DCM (1 mL) was added 1M DCM solution of acryloyl chloride (1.1 eq) dropwise, the mixture was stirred and allowed to warm to room temperature over 3 hour. LC-MS indicated formation of desired product. The mixture was concentrated and purified via prep-HPLC to afford compound 6. (10 mg). LC-MS (ESI) m/z: 217 $[M+1]^+$. 1H NMR (500 MHz, Methanol-d4) δ 8.24 (d, J=8.2 Hz, 1H), 7.40 (d, J=7.6 Hz, 1H), 7.29 (t, J=7.8 Hz, 1H), 7.22-7.07 (m, 2H), 6.89-6.66 (m, 2H), 6.43 (d, J=16.6 Hz, 1H), 5.88 (dd, J=10.5, 1.9 Hz, 1H), 4.58-4.36 (m, 3H), 3.73-3.61 (m, 1H).

Synthesis of Compound 7

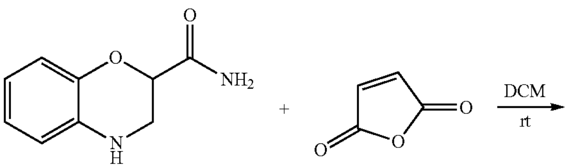

S4

-continued

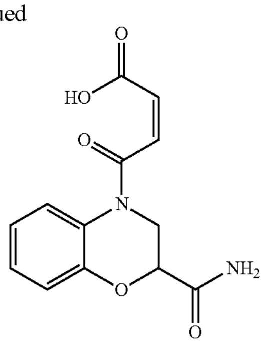

7

To mixture of S4 (80 mg) in DCM (1 mL) was added 1M DCM solution of furan-2,5-dione (1 eq) dropwise, the mixture was stirred and allowed to warm to room temperature over 3 hour. LC-MS indicated formation of desired product. The mixture was concentrated and purified via prep-HPLC to afford compound 7. (89 mg). LC-MS (ESI) m/z: 277 $[M+1]^+$. 1H NMR (500 MHz, DMSO-d6) δ 12.78 (s, 1H), 8.05 (s, 1H), 7.78-7.45 (m, 2H), 7.23-6.70 (m, 4H), 5.99 (d, J=11.7 Hz, 1H), 4.70 (d, J=63.4 Hz, 2H), 3.84 (s, 1H).

Synthesis of Compound 8

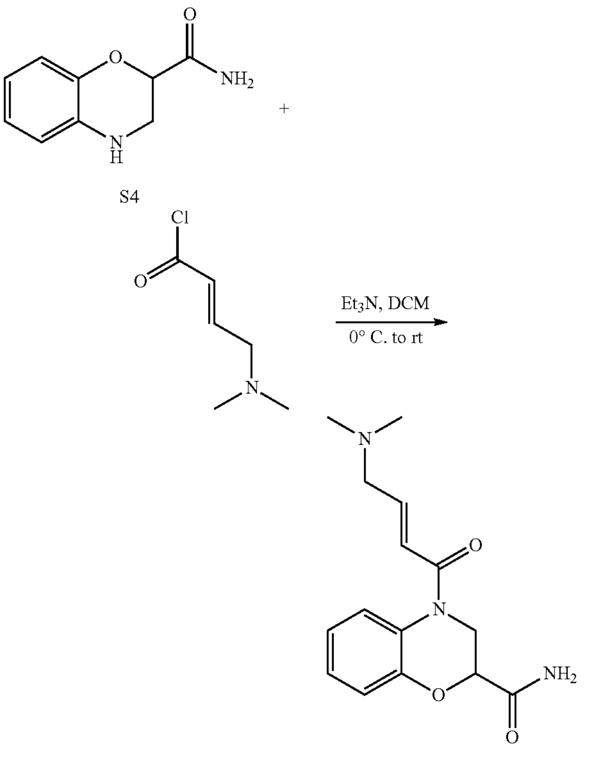

S4

8

To ice cooled mixture of S4 (15 mg) and Et3N (1.5 eq) in DCM (1 mL) was added 1M DCM solution of (E)-4-(dimethylamino)but-2-enoyl chloride (1.1 eq) dropwise, the mixture was stirred and allowed to warm to room temperature over 2 hour. LC-MS indicated formation of desired product. The mixture was concentrated and purified via prep-HPLC to afford compound 8 (19 mg). LC-MS (ESI)

m/z: 290 [M+1]+. 1H NMR (500 MHz, DMSO-d6) δ 9.85 (s, 1H), 7.62 (s, 1H), 7.46 (s, 1H), 7.15 (d, J=7.9 Hz, 1H), 7.06 (dd, J=8.2, 1.5 Hz, 1H), 6.94 (td, J=7.7, 1.5 Hz, 1H), 6.72 (s, 1H), 4.88 (t, J=4.3 Hz, 1H), 4.18 (s, 1H), 4.01-3.85 (m, 3H), 2.80 (s, 6H).

Synthesis of Compound 9

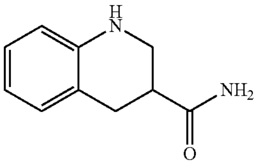
S19

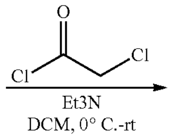

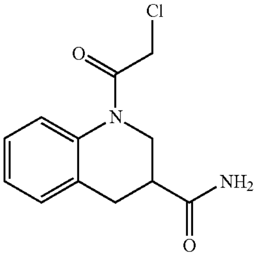
9

To mixture of S19 (20 mg) and Et3N (1.5 eq) in DCM (1 mL) was added 1M DCM solution of 2-chloroacetyl chloride (1.1 eq) dropwise at 0° C., the mixture was stirred and allowed to warm to room temperature over 1 hour. LC-MS indicated formation of desired product. The mixture was concentrated and purified via prep-HPLC to afford compound 9 (15 mg). LC-MS (ESI) m/z: 253 [M+1]+. 1H NMR (500 MHz, DMSO-d6) δ 7.53 (s, 2H), 7.27-7.11 (m, 3H), 7.06 (s, 1H), 4.56 (s, 2H), 3.92 (dd, J=13.0, 5.2 Hz, 1H), 2.98-2.72 (m, 4H).

Synthesis of Compound 10

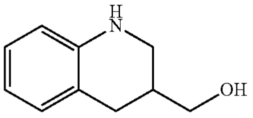
S20

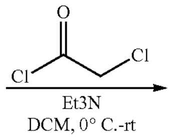

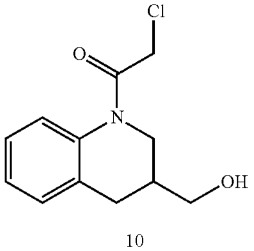
10

To mixture of S20 (15 mg) and Et3N (1.5 eq) in DCM (1 mL) was added 1M DCM solution of 2-chloroacetyl chloride (1.1 eq) dropwise at 0° C., the mixture was stirred and allowed to warm to room temperature over 1 hour. LC-MS indicated formation of desired product. The mixture was concentrated and purified via prep-HPLC to afford compound 10 (14 mg). LC-MS (ESI) m/z: 242 [M+1]+. 1H NMR (500 MHz, DMSO-d6) δ 7.09 (t, J=7.5 Hz, 1H), 6.97-6.85 (m, 2H), 4.69 (d, J=13.6 Hz, 1H), 4.58 (d, J=13.8 Hz, 1H), 4.29-4.23 (m, 1H), 3.70-3.52 (m, 4H).

Synthesis of Compound 11

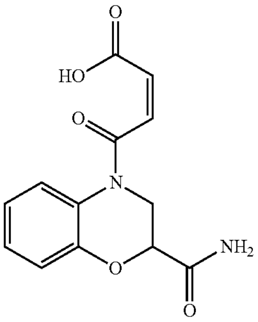
7

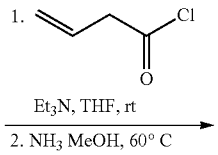

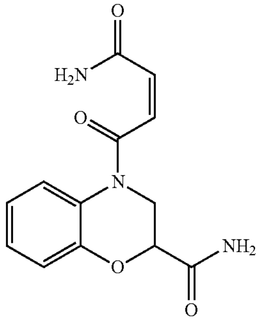
11

To mixture of compound 7 (20 mg) and Et3N (1.5 eq) in THF (1 mL) was added 1M THF solution of but-3-enoyl chloride (1.1 eq) dropwise, the mixture was stirred and allowed to warm to room temperature over 1 hour. The solvent were removed under reduced pressure. Then the mixture were dissolved in ammonia solution 7 N in methanol and heated at 60° C. for 3 hours. LC-MS indicated formation of desired product. The mixture was concentrated and purified via prep-HPLC to afford compound 11 (16 mg). LC-MS (ESI) m/z: 276 [M+1]+.

Synthesis of Compound 13

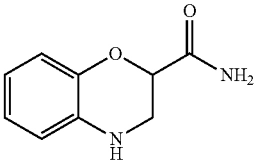
S4

+

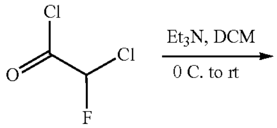

-continued

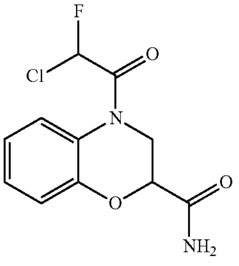

13

Compound 13: To ice cooled mixture of S4 (15 mg) and Et3N (1.5 eq) in DCM (1 mL) was added 1M DCM solution of 2-chloro-2-fluoroacetyl chloride (1.1 eq) dropwise, the mixture was stirred and allowed to warm to room temperature over 2 hour. LC-MS indicated formation of desired product. The mixture was concentrated and purified via prep-HPLC to afford compound 13 (19 mg). LC-MS (ESI) m/z: 273 $[M+1]^+$. 1H NMR (500 MHz, DMSO-d6) δ 7.72 (t, J=38.6 Hz, 3H), 7.48 (d, J=48.7 Hz, 1H), 7.17 (d, J=8.1 Hz, 1H), 7.10-7.03 (m, 1H), 7.01-6.93 (m, 1H), 4.84 (s, 1H), 4.13 (d, J=14.3 Hz, 1H), 3.81 (d, J=31.0 Hz, 1H).

Synthesis of Compound 16

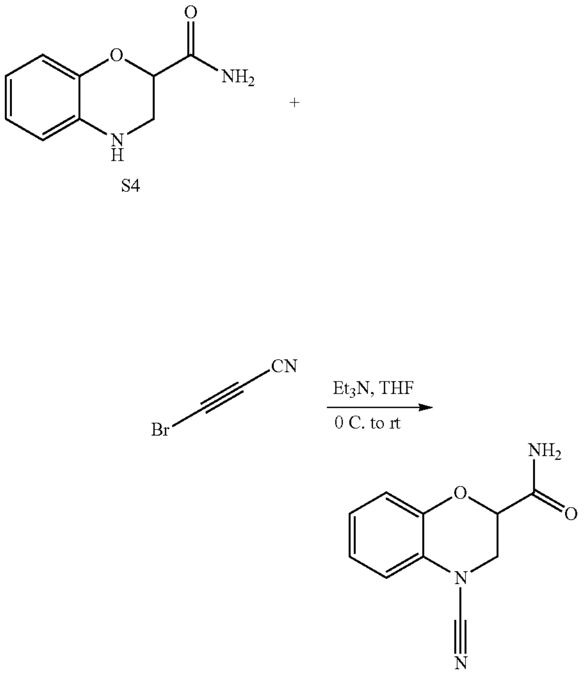

S4

16

Compound 16: To ice cooled mixture of S4 (38 mg) and Et3N (3 eq) in THF (1 mL) was added 3-bromopropiolonitrile (3 eq), the mixture was stirred and allowed to warm to room temperature over 2 hour. LC-MS indicated formation of desired product. The mixture was concentrated and purified via prep-HPLC to afford compound 16 (6 mg). LC-MS (ESI) m/z: 204 $[M+1]^+$. 1H NMR (500 MHz, DMSO-d6) δ 7.62 (d, J=27.4 Hz, 2H), 7.14-6.90 (m, 4H), 4.88 (dd, J=5.7, 3.2 Hz, 1H), 4.10-3.84 (m, 2H).

Synthesis of Compound 19

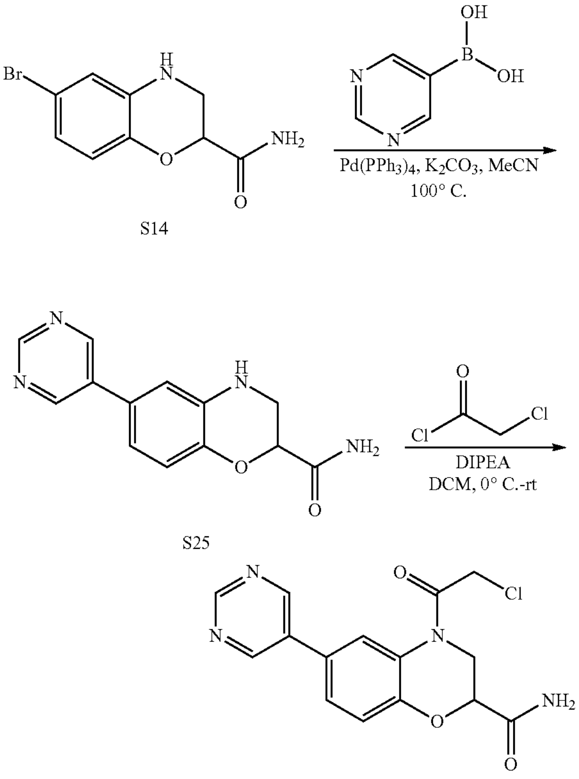

S14

S25

19

S26: The mixture of S14 (77 mg, 0.22 mmol, 1.0 eq), Pd(PPh3)4 (0.05 eq), K2CO3 (3.0 eq) and pyrimidin-5-ylboronic acid (1.0 eq) in MeCN (1 mL) under N2 protection was stirred at 100 C for 8 hours. The solution was filtered and concentrated and purified via silica gel flash chromatography to afford s26 (41 mg) as white solid LC-MS (ESI) m/z: 257 $[M+1]^+$.

Compound 19: To mixture of S26 (15 mg) and DIPEA (1.5 eq) in DCM (1 mL) was added 1M DCM solution of acryloyl chloride (1.1 eq) dropwise, the mixture was stirred and allowed to warm to room temperature over 2 hour. LC-MS indicated formation of desired product. The mixture was concentrated and purified via prep-HPLC to afford compound 19 (11 mg). LC-MS (ESI) m/z: 331 $[M+1]^+$. 1H NMR (500 MHz, DMSO-d6) δ 9.16 (s, 1H), 9.08 (s, 2H), 7.73 (s, 1H), 7.60 (s, 2H), 7.20 (d, J=8.5 Hz, 1H), 4.96 (s, 1H), 4.05 (d, J=78.3 Hz, 2H).

Synthesis of Compound 20

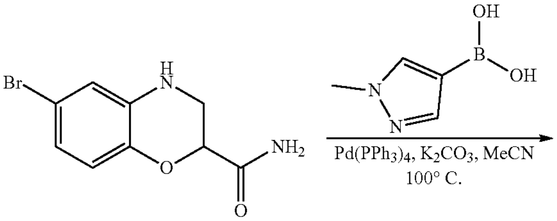

S14

-continued

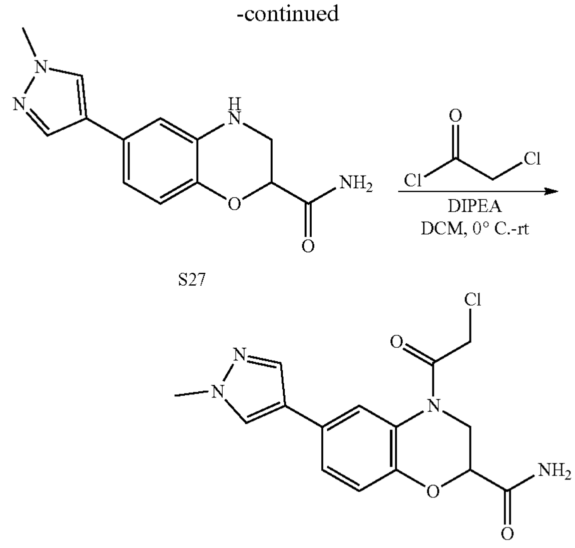

S27

20

S27: The mixture of S14 (77 mg, 1.0 eq), $Pd(PPh3)_4$ (0.05 eq), K2CO3 (3.0 eq) and (1-methyl-1H-pyrazol-4-yl)boronic acid (1.0 eq) in MeCN (1 mL) under N2 protection was stirred at 100 C for 8 hours. The solution was filtered and concentrated and purified via silica gel flash chromatography to afford s27 (39 mg) as white solid LC-MS (ESI) m/z: 259 $[M+1]^+$.

Compound 20: To mixture of S27 (17 mg) and DIPEA (1.5 eq) in DCM (1 mL) was added 1M DCM solution of acryloyl chloride (1.1 eq) dropwise, the mixture was stirred and allowed to warm to room temperature over 2 hour. LC-MS indicated formation of desired product. The mixture was concentrated and purified via prep-HPLC to afford compound 20 (11 mg). LC-MS (ESI) m/z: 335 $[M+1]^+$. 1H NMR (500 MHz, DMSO-d6) δ 8.04 (s, 1H), 7.67 (t, J=44.9 Hz, 3H), 7.37-7.29 (m, 1H), 7.02 (d, J=8.5 Hz, 1H), 4.97-4.59 (m, 4H), 4.02 (d, J=25.5 Hz, 2H), 3.85 (s, 3H).

Example 2: Biological Activity of Exemplary Compounds of the Disclosure

UCSD-AMl1 cells were suspended at 30,000 cells $mL^{-1}$ and 45 μL was added to each well of a 384 well plate (Corning 3570). To the respective well was added 5 μL of 10× stock of drug dissolved in media. After three days, 10 μL of CellTiter-Glo Luminescent Cell Viability Assay (Promega G7571) was added and incubated for 15 mins with general rocking. The plate was then read in according to manufacturer's instructions.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of Formula IV or V:

IV

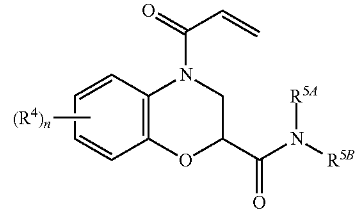

V

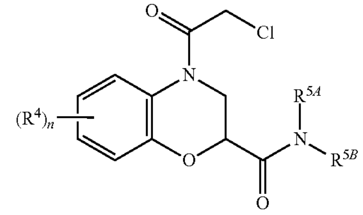

or a pharmaceutically acceptable salt thereof, wherein $R^4$ is alkyl, alkenyl, alkynyl, halo, hydroxyl, carboxyl, acyl, acetyl, ester, thioester, alkoxy, phosphoryl, amino, amide, cyano, nitro, azido, alkylthio, cycloalkyl, cycloalkylalkyl, heterocyclylalkyl, heteroaralkyl, sulfonamide, aryl, heteroaryl, heterocyclyl, or aralkyl;

$R^{5A}$ and $R^{5B}$ are each independently selected from hydrogen, alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl;

n=0-4; such that when n=0, then:

a) one of $R^{5A}$ and $R^{5B}$ in Formula IV are selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl; and b) $R^{5A}$ and $R^{5B}$ in Formula V are independently selected from alkyl, alkenyl, alkynyl, hydroxyl, carboxyl, acyl, acetyl, ester, thioester, cycloalkyl, cycloalkylalkyl, heterocyclylalkyl, heteroaralkyl, aryl, heteroaryl, heterocyclyl, and aralkyl.

2. A compound of claim 1, where n=0-1.

3. A compound of claim 2, where $R^4$ is selected from alkyl, halo, ester, and sulfonamide.

4. A compound of claim 3, where $R^{5A}$ is hydrogen and $R^{5B}$ is alkyl.

5. A compound of claim 1, where the compound is of Formula IV.

6. A compound of claim 1, where the compound is of Formula V.

7. A compound of claim 6, where n=0-1.

8. A compound of claim 7, where $R^4$ is selected from alkyl, halo, ester, and sulfonamide.

9. A compound of claim 8, where $R^{5A}$ is hydrogen and $R^{5B}$ is hydrogen or alkyl.

10. A compound of claim 1, where the compound is selected from the group consisting of:
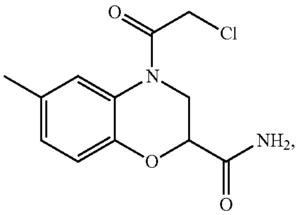
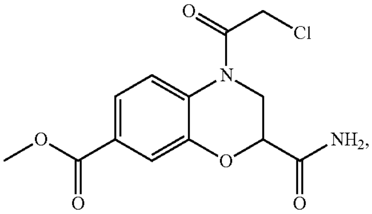
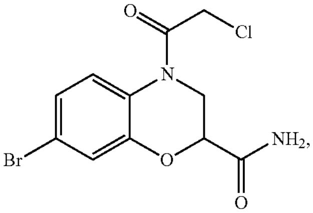
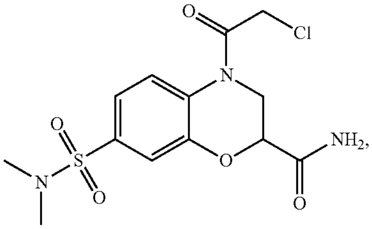
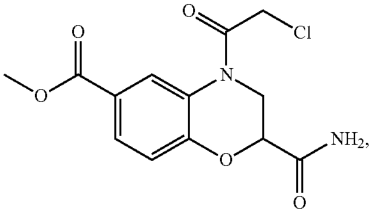
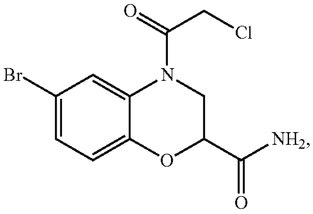
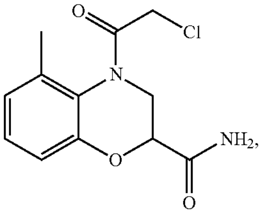
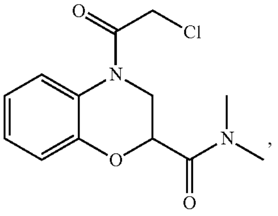
-continued
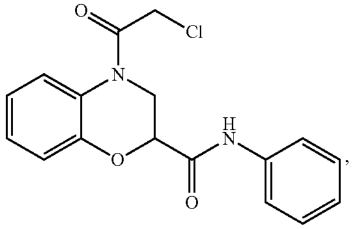
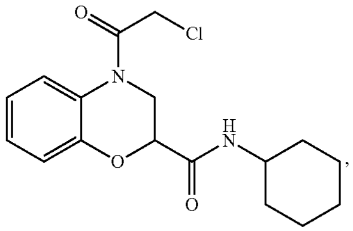
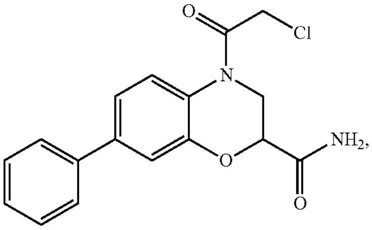
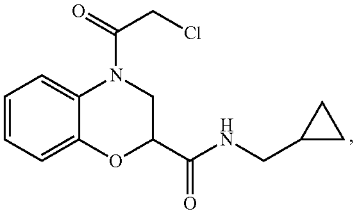
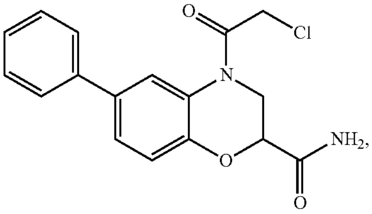
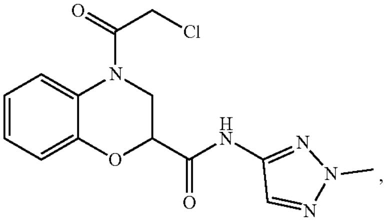
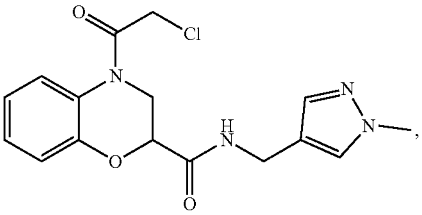

-continued
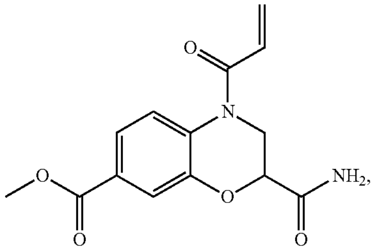
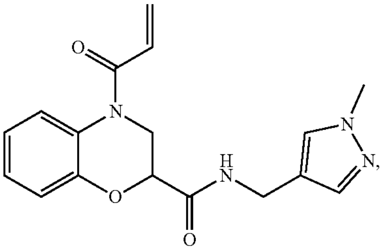
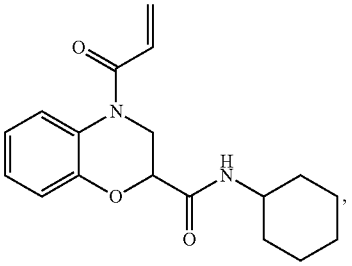
-continued
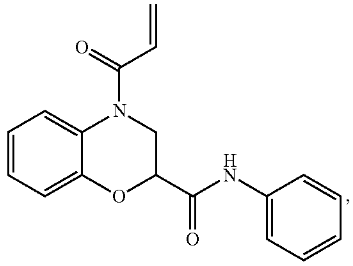
and
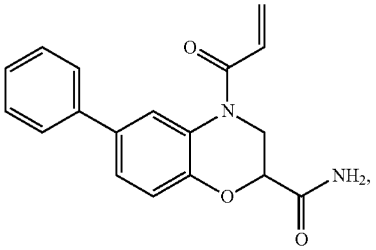
or a pharmaceutically acceptable salt thereof.
11. A pharmaceutical composition comprising a compound of claim 1 and a pharmaceutical excipient.
12. A method of treating cancer in a subject in need therefore, comprising administering a compound of claim 1 or a pharmaceutically acceptable salt thereof to the subject.
* * * * *